US012129460B2

(12) United States Patent
Calvosa et al.

(10) Patent No.: US 12,129,460 B2
(45) Date of Patent: Oct. 29, 2024

(54) METHODS FOR ETHANOL-FREE mRNA PURIFICATION

(71) Applicant: SANOFI, Paris (FR)

(72) Inventors: Eric Calvosa, Paris (FR); Nicolas Chaudet, Paris (FR); Arthur Leclercq, Paris (FR); Alban Lepetitcolin, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 18/360,978

(22) Filed: Jul. 28, 2023

(65) Prior Publication Data

US 2024/0043826 A1  Feb. 8, 2024

(30) Foreign Application Priority Data

Jul. 29, 2022  (EP) .................................... 22315175
May 15, 2023  (EP) .................................... 23173491

(51) Int. Cl.
 *C12N 15/10* (2006.01)
(52) U.S. Cl.
 CPC ....... *C12N 15/101* (2013.01); *C12N 15/1017* (2013.01)
(58) Field of Classification Search
 CPC .......................... C12N 15/101; C12N 15/1017
 USPC ....................................................... 536/25.4
 See application file for complete search history.

(56) References Cited

U.S. PATENT DOCUMENTS

| | | | |
|---|---|---|---|
| 4,373,071 A | 2/1983 | Itakura | |
| 4,401,796 A | 8/1983 | Itakura | |
| 4,415,732 A | 11/1983 | Caruthers et al. | |
| 4,458,066 A | 7/1984 | Caruthers et al. | |
| 4,500,707 A | 2/1985 | Caruthers et al. | |
| 4,668,777 A | 5/1987 | Caruthers et al. | |
| 4,973,679 A | 11/1990 | Caruthers et al. | |
| 5,047,524 A | 9/1991 | Andrus et al. | |
| 5,132,418 A | 7/1992 | Caruthers et al. | |
| 5,256,294 A | 10/1993 | Van Reis | |
| 5,490,937 A | 2/1996 | Van Reis | |
| 10,633,644 B1 | 4/2020 | Chen et al. | |
| 2011/0081708 A1 | 4/2011 | Liu et al. | |
| 2016/0032356 A1 | 2/2016 | Heartlein et al. | |
| 2018/0125989 A1 | 5/2018 | Derosa et al. | |
| 2022/0389403 A1 | 12/2022 | Derosa et al. | |

FOREIGN PATENT DOCUMENTS

| | | | |
|---|---|---|---|
| CN | 114381454 A | | 4/2022 |
| EP | 3578652 A1 | | 12/2019 |
| WO | WO 2014/140211 A1 | | 9/2014 |
| WO | WO 2014/152027 A1 | | 9/2014 |
| WO | WO 2014/152031 A1 | | 9/2014 |
| WO | WO 2014/152966 A1 | | 9/2014 |
| WO | WO 2015/164773 A1 | | 10/2015 |
| WO | WO 2016/091391 A1 | | 6/2016 |
| WO | WO 2016/174271 A1 | | 11/2016 |
| WO | WO 2016/180430 A1 | | 11/2016 |
| WO | WO 2016/193206 A1 | | 12/2016 |
| WO | WO 2017/223195 A1 | | 12/2017 |
| WO | WO 2018/157133 A1 | | 8/2018 |
| WO | WO 2018/157141 A1 | | 8/2018 |
| WO | WO 2018/157153 A1 | | 8/2018 |
| WO | WO 2020/041793 A1 | | 2/2020 |
| WO | WO 2020/097509 A1 | | 5/2020 |
| WO | WO 2020/165158 A1 | | 8/2020 |
| WO | WO 2020/232371 A1 | | 11/2020 |
| WO | WO 2021/030533 A1 | | 2/2021 |
| WO | WO 2021/209595 A2 | | 10/2021 |
| WO | WO 2022/072836 A1 | | 4/2022 |
| WO | WO 2022/104197 A1 | | 5/2022 |
| WO | WO 2022/109171 A1 | | 5/2022 |
| WO | WO 2022/121621 A1 | | 6/2022 |
| WO | WO 2022/266389 A1 | | 12/2022 |

OTHER PUBLICATIONS

BIA Separations, TN0009 "Purification of mRNA with CIMmultus™ Oligo dT", BIA Separations d.o.o., Jan. 2020, CIM Convective Interaction Media®, Technical Note, Publication # OdTinstr-2005-ebv, pp. 1-5.
Extended European Search Report for European Patent Application No. 22315175.4, dated Jan. 19, 2023.
Fechter et al., "Recognition of mRNA cap structures by viral and cellular proteins" J. Gen. Virology, 2005, 86(5): 1239-1249.
International Search Report and Written Opinion for PCT International Patent Application No., PCT/EP2023/071068, dated Nov. 6, 2023.
BIA Separations, "CIMmultus™ Oligo dT affinity column based extraction of mRNA from IVT mixtures", BIA Separations d.o.o., Poster, 2020.
BIA Separations, "Extraction of mRNA From IVT Mixtures With CIMmultus™ Oligo dT Column", BIA Separations d.o.o., A Sartorius Company, Poster, 2020.
Extended European Search Report for European Patent Application No. 24315037.2, dated Jul. 6, 2024.
Zhang et al., "Recent Advances and Innovations in the Preparation and Purification of In Vitro-Transcribed-mRNA-Based Molecules", Pharameutics, Sep. 2023, 15(9):2182. Published online Aug. 23, 2023.
BIA Separations, AN062 "Purification of messenger RNA by affinity chromatography on CIMmultus™ Oligo dT column", BIA Separations d.o.o., 2019, CIM Convective Interaction Media®,Application Note, pp. 1-3.

*Primary Examiner* — Yih-Horng Shiao
(74) *Attorney, Agent, or Firm* — LATHROP GPM LLP; James H. Velema, Esq.; Michael J. Spellberg, Esq.

(57) ABSTRACT

Provided herein are methods of purifying messenger RNA (mRNA) by subjecting a preparation comprising in vitro synthesized mRNA to one or more steps of enzymatic digestion with a proteinase, optionally with a further oligo dT affinity chromatography step. Also provided are mRNA purified by the methods described herein.

21 Claims, 9 Drawing Sheets

METHODS FOR ETHANOL-FREE mRNA PURIFICATION

BACKGROUND

Messenger RNA (mRNA)-based therapeutics have been established as an effective modality for the treatment of a variety of diseases. The mRNA molecule encodes a therapeutically relevant protein, such as an antigen for vaccination, which is produced in a subject upon administration. However, mRNA molecules are relatively large, possess a high negative charge, and are prone to degradation. In addition, the presence of contaminants remaining after mRNA purification may result in an undesirable immune response. Thus, it is important to develop effective mRNA purification strategies to ensure a highly pure, safe mRNA product that is suitable for therapeutic and preventative use. A common mRNA purification strategy employs the use of caustic or flammable solvents, such as ethanol, which is undesirable for large-scale production due to safety challenges. Accordingly, there exists a need for a flammable solvent-free, large-scale, and rapid mRNA purification scheme that yields a highly pure, safe mRNA molecule that is acceptable for therapeutic use.

SUMMARY

In one aspect, the disclosure provides a method of purifying messenger RNA (mRNA), comprising: (a) subjecting a preparation comprising in vitro synthesized mRNA to an enzymatic digestion with a proteinase; and (b) subjecting the preparation obtained from step (a) to an oligo-dT affinity chromatography.

In certain embodiments, the proteinase comprises a serine protease.

In certain embodiments, the preparation comprising in vitro synthesized mRNA is incubated with the proteinase at about 37° C. for at least 30 minutes.

In certain embodiments, the mRNA-proteinase mixture is stirred.

In certain embodiments, the proteinase is inactivated with a reducing agent, optionally wherein the reducing agent is dithiothreitol (DTT).

In certain embodiments, the DTT is added to a concentration of at least about 20 mM.

In certain embodiments, the preparation obtained from step (a) is subjected to a step of tangential flow filtration (TFF) prior to step (b).

In certain embodiments, the TFF uses about a 100 kDa to about a 300 kDa filter.

In certain embodiments, the mRNA comprised in the preparation obtained from step (a) is concentrated with the TFF.

In certain embodiments, the mRNA comprised in the preparation obtained from step (a) is concentrated to at least about 5 mg/mL.

In certain embodiments, the preparation is subjected to a step of capping prior to step (b) to produce a capped mRNA.

In certain embodiments, the preparation is incubated with 2'O-methyltransferase and guanylyltransferase.

In certain embodiments, the preparation is incubated with an RNAse inhibitor.

In certain embodiments, the preparation is incubated with GTP and S-adenosylmethionine.

In certain embodiments, capping is performed at about 37° C. for at least 30 minutes, optionally with stirring.

In certain embodiments, the preparation is subjected to a step of tailing with a poly(A) polymerase to produce a poly(A) tailed mRNA.

In certain embodiments, the preparation is co-incubated with one or more capping enzymes and a poly(A) polymerase to produce a capped and poly(A) tailed mRNA.

In certain embodiments, the preparation is incubated with one or more capping enzymes, followed by incubating the preparation with a poly(A) polymerase to produce a capped and poly(A) tailed mRNA.

In certain embodiments, the oligo dT affinity chromatography uses an oligo(dT) 25 chromatography resin.

In certain embodiments, the preparation obtained from step (b) is subjected to a step of TFF.

In certain embodiments, the TFF uses about a 50 kDa to about a 300 kDa filter.

In certain embodiments, the mRNA comprised in the preparation obtained from step (b) is concentrated with the TFF.

In certain embodiments, the mRNA comprised in the preparation obtained from step (b) is concentrated to at least about 2 mg/mL.

In one aspect, the disclosure provides a method of purifying mRNA, comprising: (a) subjecting a preparation comprising in vitro synthesized mRNA to an enzymatic digestion with a proteinase; (b) subjecting the preparation obtained from step (a) to a step of TFF; (c) subjecting the preparation obtained from step (b) to an oligo dT affinity chromatography; and (d) subjecting the preparation obtained from step (c) to a step of TFF.

In certain embodiments, the preparation obtained from step (b) is incubated with one or more capping enzymes to produce a capped mRNA.

In certain embodiments, the preparation obtained from step (b) is incubated with a poly(A) polymerase to produce a poly(A) tailed mRNA.

In certain embodiments, the preparation obtained from step (b) is co-incubated with one or more capping enzymes and a poly(A) polymerase to produce a capped and poly(A) tailed mRNA.

In one aspect, the disclosure provides a method of purifying mRNA, comprising: (a) subjecting a preparation comprising in vitro synthesized mRNA to a first enzymatic digestion with a proteinase; (b) subjecting the preparation obtained from step (a) to a second enzymatic digestion with a proteinase; and (c) subjecting the preparation obtained from step (b) to a step of TFF.

In certain embodiments, the proteinase comprises a serine protease.

In certain embodiments, the first enzymatic digestion and/or the second enzymatic digestion occurs at about 37° C. for at least 30 minutes.

In certain embodiments, the first enzymatic digestion and/or the second enzymatic digestion is stirred.

In certain embodiments, the proteinase is inactivated with a reducing agent, optionally wherein the reducing agent is DTT.

In certain embodiments, the DTT is added to a concentration of at least about 20 mM.

In certain embodiments of any of the methods described above, no precipitation step is performed.

In certain embodiments of any of the methods described above, at least about 0.5 grams of mRNA is purified.

In certain embodiments of any of the methods described above, about 0.5 grams to about 100 grams of mRNA is purified.

In certain embodiments of any of the methods described above, the preparation is subjected to a step of frontal filtration after capping.

In certain embodiments of any of the methods described above, the preparation is subjected to a step of frontal filtration prior to the step of oligo dT affinity chromatography.

In certain embodiments of any of the methods described above, the preparation is subjected to a step of frontal filtration after capping and prior to the step of oligo dT affinity chromatography.

In certain embodiments, the filter used for frontal filtration is a 0.2 µm filter.

In one aspect, the disclosure provides a method for manufacturing mRNA comprising: synthesizing mRNA in vitro; and purifying the in vitro synthesized mRNA using a method described above.

In another aspect, the disclosure provides a mRNA obtainable by a method described above.

BRIEF DESCRIPTION OF THE DRAWINGS

The foregoing and other features and advantages of the present disclosure will be more fully understood from the following detailed description of illustrative embodiments taken in conjunction with the accompanying drawings.

DETAILED DESCRIPTION

Figure 1:
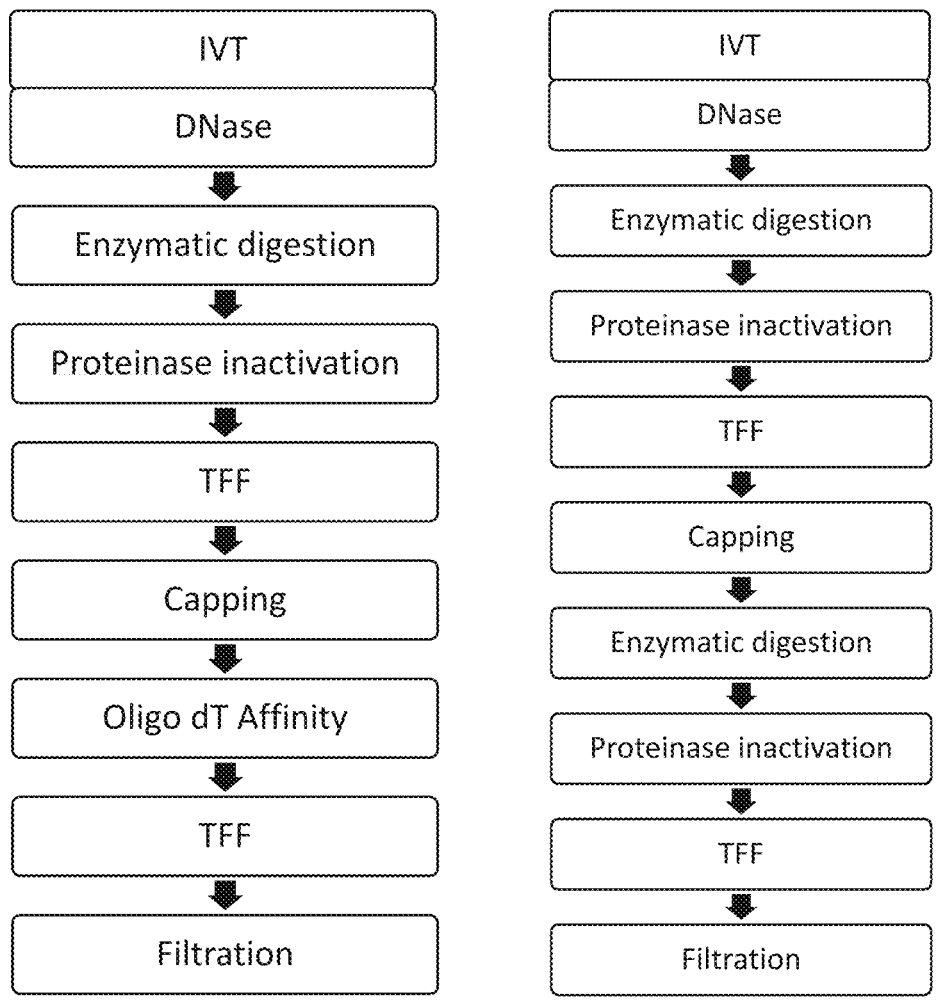
FIG. 1 shows a flow chart outlining exemplary steps of the ethanol-free purification methods. The ethanol-free purification methods may use both enzymatic digestion and affinity chromatography (enzymatic/affinity method; left panel) or only enzymatic digestion (full enzymatic method; right panel).

The present disclosure is directed to, inter alia, methods of mRNA purification by subjecting a preparation comprising in vitro synthesized mRNA to one or more steps of enzymatic digestion with a proteinase, optionally with a further oligo dT affinity chromatography step.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, virology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art.

It is to be noted that the term "a" or "an" entity refers to one or more of that entity; for example, "a nucleotide sequence" is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, may provide one of skill with a general dictionary of many of the terms used in this disclosure.

Units, prefixes, and symbols are denoted in their International System of Units (SI) accepted form. Numeric ranges are inclusive of the numbers defining the range. The headings provided herein are not limitations of the various aspects of the disclosure. Accordingly, the terms defined immediately below are more fully defined by reference to the specification in its entirety.

The term "approximately" or "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower). In some embodiments, the term indicates deviation from the indicated numerical value by ±10%, ±5%, ±4%, ±3%, ±2%, ±1%, ±0.9%, ±0.8%, ±0.7%, ±0.6%, ±0.5%, ±0.4%, ±0.3%, ±0.2%, ±0.1%, ±0.05%, or ±0.01%. In some embodiments, "about" indicates deviation from the indicated numerical value by ±10%. In some embodiments, "about" indicates deviation from the indicated numerical value by ±5%. In some embodiments, "about" indicates deviation from the indicated numerical value by ±4%. In some embodiments, "about" indicates deviation from the indicated numerical value by ±3%. In some embodiments, "about" indicates deviation from the indicated numerical value by ±2%. In some embodiments, "about" indicates deviation from the indicated numerical value by ±1%. In some embodiments, "about" indicates deviation from the indicated numerical value by ±0.9%. In some embodiments, "about" indicates deviation from the indicated numerical value by ±0.8%. In some embodiments, "about" indicates deviation from the indicated numerical value by ±0.7%. In some embodiments, "about" indicates deviation from the indicated numerical value by ±0.6%. In some embodiments, "about" indicates deviation from the indicated numerical value by ±0.5%. In some embodiments, "about" indicates deviation from the indicated numerical value by ±0.4%. In some embodiments, "about" indicates deviation from the indicated numerical value by ±0.3%. In some embodiments, "about" indicates deviation from the indicated numerical value by ±0.1%. In some embodiments, "about" indicates deviation from the indicated numerical value by ±0.05%. In some embodiments, "about" indicates deviation from the indicated numerical value by ±0.01%.

As used herein, the term "batch" refers to a quantity or amount of mRNA purified at one time, e.g., purified according to a single manufacturing order during the same cycle of manufacture. A batch may refer to an amount of mRNA purified in a single purification run.

As used herein, the terms "subjected to" or "contacted" or "incubated" refer to the mixing of two or more components such that those components are capable of interacting (e.g., incubating a preparation comprising in vitro synthesized mRNA with a proteinase). The two or more components may be incubated for any time sufficient to produce a desired effect.

As used herein, a "method of purifying" refers to a method of obtaining target molecules from a mixture, e.g., a solution or suspension, comprising said target molecules to be purified and components other than the target molecules, wherein the concentration of the target molecules is enhanced or increased in the solution obtained after performing said method compared to the concentration of the target molecules in the mixture before performing said method. The purification of target molecules can also be referred to as the enrichment of said target molecules by removing or at least substantially removing components other than the target molecules. In the context of the present invention, the target molecules are mRNA molecules.

More particularly, the present invention relates to a method of purifying mRNA, comprising:
 (a) subjecting a preparation comprising mRNA to an enzymatic digestion with a proteinase; and
 (b) subjecting the preparation obtained from step (a) to an oligo dT affinity chromatography.

As used herein, the term "messenger RNA" or "mRNA" refers to a polynucleotide that encodes at least one polypeptide. mRNA may contain one or more coding and non-coding regions. A coding region is alternatively referred to as an open reading frame (ORF).

mRNA as used herein encompasses both modified and unmodified RNA. In some embodiments, the mRNA may comprise at least one chemical modification. In some embodiments, the mRNA may contain one or more modifications that typically enhance RNA stability. A modified mRNA as provided herein can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotide analogues or derivatives of purines and pyrimidines, such as e.g. 1-methyl-adenine, 2-methyladenine, 2-methylthio-N-6-isopentenyl-adenine, N6-methyladenine, N6-isopentenyladenine, 2-thiocytosine, 3-methylcytosine, 4-acetylcytosine, 5-methylcytosine, 2,6-diaminopurine, 1-methylguanine, 2-methylguanine, 2,2-dimethylguanine, 7-methylguanine, inosine, 1-methylinosine, pseudouracil (5-uracil), dihydrouracil, 2-thiouracil, 4-thiouracil, 5-carboxymethylaminomethyl-2-thiouracil, 5-(carboxyhydroxymethyl)-uracil, 5-fluorouracil, 5-bromouracil, 5-carboxymethylaminomethyluracil, 5-methyl-2-thiouracil, 5-methyluracil, N-uracil-5-oxyacetic acid methyl ester, 5-methylaminomethyl-uracil, 5-methoxyaminomethyl-2-thiouracil, 5'-methoxycarbonylmethyl-uracil, 5-methoxyuracil, uracil-5-oxyacetic acid methyl ester, uracil-5-oxyacetic acid (v), 1-methyl-pseudouracil, queosine, β-D-mannosyl-queosine, wybutoxosine, and phosphoramidates, phosphorothioates, peptide nucleotides, methylphosphonates, 7-deazaguanosine, 5-methylcytosine, and inosine.

In some embodiments, the mRNA may comprise at least one chemical modification including, but not limited to, pseudouridine, N1-methylpseudouridine, 2-thiouridine, 4'-thiouridine, 5-methylcytosine, 2-thio-I-methyl-1-deazapseudouridine, 2-thio-I-methylpseudouridine, 2-thio-5-aza-uridine, 2-thio-dihydropseudouridine, 2-thio-dihydrouridine, 2-thiopseudouridine, 4-methoxy-2-thio-pseudouridine, 4-methoxy-pseudouridine, 4-thio-I-methylpseudouridine, 4-thio-pseudouridine, 5-aza-uridine, dihydropseudouridine, 5-methyluridine, 5-methyluridine, 5-methoxyuridine, and 2'-O-methyl uridine.

In some embodiments, the chemical modification is selected from the group consisting of pseudouridine, N1-methylpseudouridine, 5-methylcytosine, 5-methoxyuridine, and any combination thereof. In some embodiments, the chemical modification comprises N1-methylpseudouridine.

In some embodiments, at least 20%, at least 30%, at least 40%, at least 50%, at least 60%, at least 70%, at least 80%, at least 85%, at least 90%, at least 95%, or 100% of the uracil nucleotides in the mRNA are chemically modified.

In some embodiments, at least 20%, at least 30%, at least 40%, at least 50%, at least 60%, at least 70%, at least 80%, at least 85%, at least 90%, at least 95%, or 100% of the uracil nucleotides in the ORF are chemically modified.

The preparation of such analogues is described, e.g., in U.S. Pat. Nos. 4,373,071, 4,401,796, 4,415,732, 4,458,066, 4,500,707, 4,668,777, 4,973,679, 5,047,524, 5,132,418.

mRNA can be synthesized in a cell-free environment, for example by in vitro transcription (IVT). IVT is a process that permits template-directed synthesis of ribonucleic acid (RNA) (e.g., mRNA). In vitro transcription (IVT) is typically performed with a linear or circular DNA template comprising a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application. Accordingly, in some embodiments, manufacturing the mRNA comprises the steps of performing IVT by mixing (i) a DNA template comprising a suitable promoter and (ii) an RNA polymerase, to generate an impure preparation comprising full-length mRNA which is then subjected to the purification methods disclosed herein. The presence of these reagents is undesirable in a final mRNA product and they may thus be referred to as impurities which may be purified or removed to provide a clean and/or homogeneous mRNA that is suitable for therapeutic use.

In some embodiments, the DNA template is a linear DNA template. In some embodiments, the DNA template is a circular DNA template. In some embodiments, the DNA template is a PCR-amplified DNA molecule. The invention is not limited with respect to the RNA polymerase that is used for transcription. For example, in some embodiments, a T7, T3, or SP6-type RNA polymerase can be used. In some embodiments, the polymerase is T7 polymerase. In some embodiments, the polymerase is SP6 polymerase. In some embodiments, the in vitro transcription further includes mixing a pool of ribonucleotide triphosphates.

In some embodiments, the DNA template to be transcribed may be optimized to facilitate more efficient transcription and/or translation. For example, the DNA template may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA template may be optimized regarding cryptic splice sites, mRNA secondary structure, stable free energy of mRNA, repetitive sequences, mRNA instability motif, and/or other elements relevant to mRNA processing and stability; the DNA template may be optimized regarding codon usage bias, codon adaptability, internal chi sites, ribosomal binding sites (e.g., IRES), premature poly(A)

sites, Shine-Dalgarno (SD) sequences, and/or other elements relevant to translation; and/or the DNA template may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which is described in US 20110081708, the contents of which are incorporated herein by reference in its entirety.

The inventors found that a precipitate may form during the in vitro transcription process. In some instances, most of the synthesized mRNA is present in this precipitate, with a low concentration of mRNA present in the supernatant (see Example 10). Surprisingly, the precipitate could not be resolubilized by dilution in water, by dilution in buffer, or by decreasing the pH of the preparation.

The inventors tested the addition of 10 mM, 25 mM or 50 mM sodium citrate to the preparation comprising in vitro synthesized mRNA. A significant reduction in turbidity was observed following the addition of 10 mM sodium citrate, and complete resolubilization of the precipitate following the addition of 25 mM or 50 mM sodium citrate. Accordingly, in some embodiments, sodium citrate is added to the preparation comprising in vitro synthesized mRNA after the mRNA is subjected to enzymatic digestion with a proteinase. In some embodiments sodium citrate is added to the preparation comprising in vitro synthesized mRNA at a concentration of at least about 10 mM, optionally at least about 25 mM. In particular embodiments, sodium citrate is added to the preparation comprising in vitro synthesized mRNA at a concentration of about 25 mM. The preparation may be incubated with sodium citrate for at least about five minutes. The preparation is optionally at about 37° C. (e.g., 35-37° C.) prior to addition of sodium citrate. Alternatively, the preparation is optionally held at about 35° C. to about 37° C. for at least about 5 minutes following the addition of sodium citrate.

The inventors also tested the addition of EDTA to the preparation comprising in vitro synthesized mRNA, and observed complete resolubilization of the precipitate with mM EDTA. Accordingly, in some embodiments, EDTA is added to the preparation comprising in vitro synthesized mRNA after the mRNA is subjected to enzymatic digestion with a proteinase. In some embodiments, EDTA is added to the preparation comprising in vitro synthesized mRNA at a concentration of at least about 10 mM, optionally at least about mM. In particular embodiments, EDTA is added to the preparation comprising in vitro synthesized mRNA at a concentration of about 25 mM. The preparation may be incubated with EDTA for at least about five minutes. The preparation is optionally at about 37° C. (e.g., 35-37° C.) prior to addition of EDTA. Alternatively, the preparation is optionally held at about ° C. to about 37° C. for at least about 5 minutes following the addition of EDTA.

As used herein, the term "shortmers" or "prematurely aborted RNA sequences" refers to incomplete products of an mRNA synthesis reaction (e.g., an in vitro synthesis reaction). For a variety of reasons, RNA polymerases do not always complete transcription of a DNA template; e.g., RNA synthesis terminates prematurely. Possible causes of premature termination of RNA synthesis include quality of the DNA template, polymerase terminator sequences for a particular polymerase present in the template, degraded buffers, temperature, depletion of ribonucleotides, and mRNA secondary structures. Prematurely aborted RNA sequences may be any length that is less than the intended length of the desired transcriptional product. For example, prematurely aborted mRNA sequences may be less than 1000 bases, less than 500 bases, less than 100 bases, less than 50 bases, less than 40 bases, less than 30 bases, less than 20 bases, less than 15 bases, less than bases or fewer.

Double-stranded RNA (dsRNA) may also be formed during in vitro synthesis of mRNA (e.g., when the 3' end of a full-length RNA transcript hybridizes with itself). This is undesirable, because dsRNA can have an immune-stimulatory effect. It is challenging to remove dsRNA contamination from an mRNA product due to their similar sizes and intrinsic characteristics. RNase III (also known as RNase C) may be used to digest dsRNA in the presence of the desired mRNA product to facilitate its removal. However, RNase III can also digest the desired mRNA product, so often lowers the percentage of intact mRNA, and additional method steps are required to clear RNase III from the mRNA preparation.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "substantially free" refers to a state in which relatively little or no amount of a substance to be removed (e.g., prematurely aborted RNA sequences) are present. For example, "substantially free of prematurely aborted RNA sequences" means the prematurely aborted RNA sequences are present at a level less than approximately 5%, 4%, 3%, 2%, 1.0%, 0.9%, 0.8%, 0.7%, 0.6%, 0.5%, 0.4%, 0.3%, 0.1% or less (w/w) of the impurity. Alternatively, "substantially free of prematurely aborted RNA sequences" means the prematurely aborted RNA sequences are present at a level less than about 100 ng, 90 ng, 80 ng, 70 ng, 60 ng, 50 ng, 40 ng, 30 ng, 20 ng, 10 ng, 1 ng, 500 pg, 100 pg, 50 µg, 10 pg, or less.

In one embodiment, a method of purifying mRNA is provided, comprising:
  (a) subjecting a preparation comprising in vitro synthesized mRNA to an enzymatic digestion with a proteinase; and
  (b) subjecting the preparation obtained from step (a) to an oligo dT affinity chromatography.

The present invention can be used to purify mRNAs that encode any protein. Typically, the present invention is used to purify a single mRNA species, i.e., the preparation comprising mRNA contains mRNA derived from a single gene, a single synthesis reaction, or a single expression construct. In contrast, total mRNA purified from a cell contains multiple mRNA species. While mRNA provided from in vitro transcription reactions may be desirable in some embodiments, other sources of mRNA are contemplated as within the scope of the invention including wild-type mRNA produced from bacteria, fungi, plants, and/or animals.

As used herein, the term "in vitro" refers to events that occur in an artificial environment, e.g., in a test tube or reaction vessel, in cell culture, etc., rather than within a multi-cellular organism.

According to various embodiments, the present invention is used to purify in vitro synthesized mRNA of a variety of lengths. In some embodiments, the present invention is used to purify in vitro synthesized mRNA of greater than about 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, or 15 kb in length. In some embodiments, the present invention is used to purify mRNA containing one or more modifications that typically enhance stability. In some embodiments, one or more modifications are selected from modified nucleotide, such as those described herein, and modified sugar phosphate backbones, In some embodiments, the present invention is used to purify in vitro synthesized mRNA that is unmodified.

Typically, mRNA comprises a 5' cap structure. An mRNA 5' cap can provide resistance to nucleases found in most eukaryotic cells and promote translation efficiency. Several types of 5' caps are known. A 7-methylguanosine cap (also referred to as "m7G" or "Cap-0"), comprises a guanosine that is linked through a 5'-5'-triphosphate bond to the first transcribed nucleotide.

The term "capping" refers to the addition of a 5' cap structure to the mRNA. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp, (5'(A,G(5')ppp(5')A, and G(5')ppp (5')G. Additional cap structures are described in U.S. Publication No. US 2016/0032356 and U.S. Publication No. US 2018/0125989, which are incorporated herein by reference.

5'-capping may be completed concomitantly during the IVT reaction using a cap analog, which can be incorporated as the first "base" in a nascent RNA strand. The cap analog may be Cap 0, Cap 1, Cap 2, m6Am, or a cap analog. As an example, the following chemical RNA cap analogs may be used to generate the 5'-guanosine cap structure according to the manufacturer's instructions: 3'-O-Me-m7G(5')ppp(5')G (the ARCA cap); G(5')ppp(5')A; G(5')ppp(5')G; m7G(5')ppp (5')A; m7G(5')ppp(5')G; m7G(5')ppp(5)(2'OMeA)-pG; m7G(5')ppp(5')(2'OMeA)pU; m7G(5')ppp(5')(2'OMeG)pG (New England BioLabs, Ipswich, MA; TriLink Biotechnologies).

Alternatively, capping of the mRNA may be performed post-transcriptionally (i.e., after IVT). For example, a vaccinia virus capping enzyme may be used to generate the Cap 0 structure: m7G(5')ppp(5')G. Cap 1 structure may be generated using both vaccinia virus capping enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase.

In some embodiments, the mRNA comprises a 5' cap selected from the group consisting of 3'-O-Me-m7G(5')ppp(5')G (the ARCA cap), G(5')ppp(5')A, G(5')ppp(5')G, m7G(5')ppp(5')A, m7G(5')ppp(5')G, m7G(5')ppp(5)(2'OMeA)pG, m7G(5')ppp(5)(2'OMeA)pU, and m7G(5')ppp(5)(2'OMeG)pG. In certain embodiments, the mRNA comprises a 5' cap of:

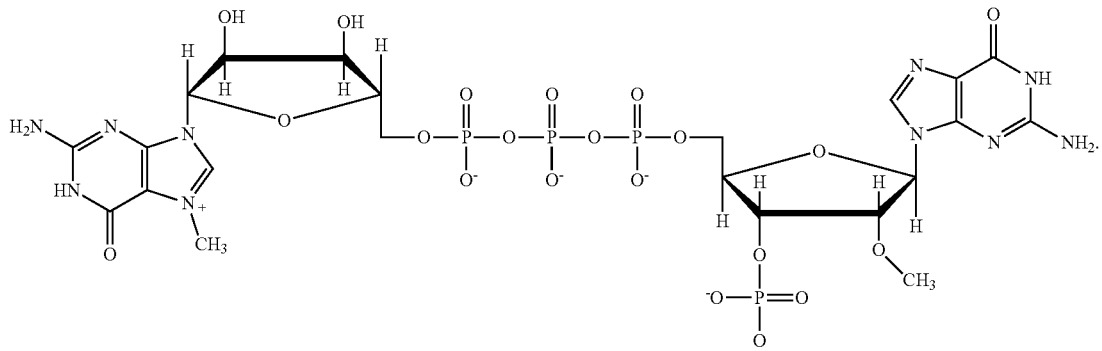

A "capping enzyme" refers to an enzyme that catalyzes the attachment of the 5' cap to mRNA. A single capping enzyme comprising the enzymatic activities that are necessary for capping may be used. Alternatively, two or more enzymes having different enzymatic activities may be used, such as 2'O-methyltransferase and guanylyl transferase. Capping may occur in the presence of an RNAse inhibitor, the methyl donor S-adenosylmethionine, and/or GTP.

In some embodiments, mRNA include a 5' and/or 3' untranslated region (UTR). In some embodiments, a 5' UTR includes one or more elements that affect an mRNAs stability or translation, for example, an iron responsive element. Exemplary 5' and/or 3' UTR sequences can be derived from mRNA molecules which are stable (e.g., globin, actin, GAPDH, tubulin, histone, and citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of mRNA.

In some embodiments, a 5' UTR may be between about 50 and 500 nucleotides in length. In some embodiments, a 3' UTR includes one or more of a polyadenylation signal, a binding site for proteins that affect an mRNAs stability of location in a cell, or one or more binding sites for miRNAs. In some embodiments, a 3' UTR may be between 50 and 500 nucleotides in length or longer.

Typically, mRNA comprises a poly(A) tail. As used herein, the terms "poly(A) sequence," "poly(A) tail," and "poly(A) moiety" refer to a sequence of adenosine nucleotides at the 3' end of the mRNA molecule. The poly(A) tail may confer stability to the mRNA and protect it from exonuclease degradation. The poly(A) tail may enhance translation. In some embodiments, the poly(A) tail is essentially homopolymeric. For example, a poly(A) tail of 100 adenosine nucleotides may have essentially a length of 100 nucleotides. When the mRNA comprises a 3' UTR, the poly(A) tail may be directly downstream of the coding region (i.e., before the 3' UTR) or downstream of the 3' UTR. A poly(A) tail may contain 10 to 500 adenosine monophosphates. For example, a poly(A) tail may contain at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500, adenosine monophosphates. In some embodiments, a poly(A) tail contains 20 to 300 adenosine monophosphates. In some embodiments, a poly(A) tail contains 50 to 250 adenosine monophosphates. In some embodiments, a poly(A) tail contains 75 to 225 adenosine monophosphates. In some embodiments, a poly(A) tail contains 90 to 200 adenosine monophosphates. In some embodiments, a poly(A) tail contains 100 to 150 adenosine monophosphates. In some embodiments, a poly(A) tail contains at least 100 adenosine monophosphates. In some embodiments, a poly(A) tail contains at least 150 adenosine monophosphates. In some embodiments, a poly(A) tail contains at least 200 adenosine monophosphates. In some embodiments, a poly(A) tail contains at least 250 adenosine monophosphates. In some embodiments, a poly(A) tail contains at least 300 adenosine monophosphates. In some embodiments, a poly(A) tail contains at least 350 adenosine monophosphates. In some embodiments, a poly(A) tail contains at least 400 adenosine monophosphates. In some embodiments, a poly(A) tail contains at least 450 adenosine monophosphates. In certain embodiments, the poly(A) tail may be interrupted by at least one nucleotide different from an adenosine nucleotide (e.g., a nucleotide that is not an adenosine nucleotide). For example, a poly(A) tail of 100 adenosine nucleotides may have a length of more than 100 nucleotides (comprising 100 adenosine nucleotides and at least one nucleotide, or a stretch of nucleotides, that are different from an adenosine nucleotide).

In some embodiments, the poly(A) tail of the nucleic acid is obtained from a DNA template during RNA in vitro transcription. In certain embodiments, the poly(A) tail is obtained in vitro by common methods of chemical synthesis without being transcribed from a DNA template. In various embodiments, poly(A) tails are generated by enzymatic polyadenylation of the RNA (after RNA in vitro transcription) using commercially available polyadenylation kits and corresponding protocols, or alternatively, by using immobilized poly(A) polymerases, e.g., using methods and means as described in WO2016/174271.

The nucleic acid may comprise a poly(A) tail obtained by enzymatic polyadenylation, wherein the majority of nucleic acid molecules comprise about 100 (+/−20) to about 500 (+/−50) or about 250 (+/−20) adenosine nucleotides.

In some embodiments, the nucleic acid may comprise a poly(A) tail derived from a template DNA and may additionally comprise at least one additional poly(A) tail generated by enzymatic polyadenylation, e.g., as described in WO2016/091391.

As used herein, the term "proteinase" refers to a protease that catalyzes the hydrolytic breakdown of proteins by splitting them into smaller peptide fractions, i.e., polypeptides or amino acids. In other words, a proteinase enzymatically digests proteins or polypeptides. Examples of proteinases or proteases include, but are not limited to, serine proteases (e.g., proteinase K), cysteine proteases, threonine proteases, aspartic proteases, glutamic proteases, metalloproteases, and asparagine peptide lyases.

"Isolated," "isolating," "purified," "purifying," "enriched," and "enriching," when used with respect to an mRNA of interest, indicate that the mRNA of interest at some point in time was separated, enriched, sorted, etc., from or with respect to other biological material or chemical components, such as components of an IVT reaction, to yield a higher proportion of the mRNA of interest compared to the other biological material, chemical components, contaminates, or active agents such as enzymes. Isolated mRNA may be separated from about 10%, about 20%, about 30%, about 40%, about 50%, about 60%, about 65%, about 70%, about 75%, about 80%, about 85%, about 90%, about 91%, about 92%, about 93%, about 94%, about 95%, about 96%, about 97%, about 98%, about 99%, or more than about 99% of the other components with which it was initially associated. In some embodiments, isolated mRNA is about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Components from which mRNA may be isolated notably include dsRNA, plasmid DNA, enzymes, and endotoxins. As used herein, calculation of percent purity of isolated substances should not include excipients (e.g., buffer, water, etc.).

In some embodiments, less than 10 pg/mg (e.g., less than 10 pg/mg, less than 9 pg/mg, less than 8 pg/mg, less than 7 pg/mg, less than 6 pg/mg, less than 5 pg/mg, less than 4 pg/mg, less than 3 pg/mg, less than 2 pg/mg, or less than 1 pg/mg) is an acceptable level of residual plasmid DNA. In some embodiments, the residual plasmid DNA in the purified mRNA of the present invention is less than about 1 pg/mg, less than about 2 pg/mg, less than about 3 pg/mg, less than about 4 pg/mg, less than about 5 pg/mg, less than about 6 pg/mg, less than about 7 pg/mg, less than about 8 pg/mg, less than about 9 pg/mg, less than about 10 pg/mg, less than about 11 pg/mg, or less than about 12 pg/mg. Accordingly, the residual plasmid DNA in the purified mRNA is less than about 1 pg/mg. In some embodiments, the residual plasmid DNA in the purified mRNA is less than about 2 pg/mg. In some embodiments, the residual plasmid DNA in the purified mRNA is less than about 3 pg/mg. In some embodiments, the residual plasmid DNA in the purified mRNA is less than about 4 pg/mg. In some embodiments, the residual plasmid DNA in the purified mRNA is less than about 5 pg/mg. In some embodiments, the residual plasmid DNA in the purified mRNA is less than about 6 pg/mg. In some embodiments, the residual plasmid DNA in the purified mRNA is less than about 7 pg/mg. In some embodiments, the residual plasmid DNA in the purified mRNA is less than about 8 pg/mg. In some embodiments, the residual plasmid DNA in the purified mRNA is less than about 9 pg/mg. In some embodiments, the residual plasmid DNA in the purified mRNA is less than about 10 pg/mg.

The inventors have shown that residual plasmid DNA can be effectively removed from large batches of mRNA using the methods provided herein. In some embodiments, in vitro synthesized mRNA is purified at a scale of or greater than about 10 gram per batch, and the residual plasmid DNA in the purified mRNA is less than about 0.5 pg/mg (e.g., less than about 0.2 pg/mg). In some embodiments, in vitro synthesized mRNA is purified at a scale of or greater than about 20 gram per batch, and the residual plasmid DNA in the purified mRNA is less than about 0.5 pg/mg (e.g., less than about 0.2 pg/mg). In some embodiments, residual plasmid DNA is assessed by methods in the art, for example by the use of qPCR.

In some embodiments, a method according to the invention removes more than about 80%, 85%, 90%, 95%, 96%, 97%, 98%, 99% or substantially all prematurely aborted RNA sequences. In some embodiments, mRNA composition is substantially free of prematurely aborted RNA sequences. In some embodiments, mRNA composition contains less than about 5% (e.g., less than about 4%, 3%, 2%, or 1%) of prematurely aborted RNA sequences. In some embodiments, mRNA composition contains less than about 1% (e.g., less than about 0.9%, 0.8%, 0.7%, 0.6%, 0.5%, 0.4%, 0.3%, 0.2%, or 0.1%) of prematurely aborted RNA sequences. In some embodiments, the mRNA isolated according to a method of the present invention contains undetectable prematurely aborted RNA sequences as determined by, e.g., high-performance liquid chromatography (HPLC) (e.g., shoulders or separate peaks), ethidium bromide, Coomassie staining, capillary electrophoresis (CE) or Glyoxal gel electrophoresis (e.g., presence of separate lower band). In some embodiments, prematurely aborted RNA sequences are less than 1000 bases, less than 500 bases, less than 100 bases, less than 90 bases, less than 80 bases, less than 70 bases, less than 60 bases, less than 50 bases, less than 40 bases, less than 30 bases, less than bases, or less than 10 bases in length. In some embodiments, shortmers are detected or quantified after adding a 5'-cap, and/or a 3'-poly A tail. In some embodiments, prematurely aborted RNA transcripts comprise less than 15 bases (e.g., less than 14, 13, 12, 11, 10, 9, 8, 7, 6, 5, 4, or 3 bases). In some embodiments, the prematurely aborted RNA transcripts contain about 8-15, 8-14, 8-13, 8-12, 8-11, or 8-10 bases.

The inventors have shown that double-stranded RNA (dsRNA) can also be effectively removed from large batches of mRNA using the methods provided herein. In some embodiments, the purified mRNA contains less than about 1% (e.g., less than about 0.2%, or 0.1%) of dsRNA. In some embodiments, the purified mRNA contains less than about 0.1% (e.g., less than about 0.05%, 0.03%, 0.025%, or 0.01%) of dsRNA. In some embodiments, dsRNA level is assessed by methods in the art, for example ELISA or dot blot using the anti-dsRNA monoclonal antibody J2. In some embodiments, the method does not comprise a step of contacting the preparation with an RNase III.

In some embodiments, in vitro synthesized mRNA is purified at a scale of or greater than about 10 gram per batch, and the purified mRNA composition contains less than about 0.1% dsRNA. In some embodiments, in vitro synthesized mRNA is purified at a scale of or greater than about 10 gram per batch, and the purified mRNA composition contains less than about 0.01% dsRNA. In some embodiments, in vitro synthesized mRNA is purified at a scale of or greater than about 20 gram per batch, and the purified mRNA composition contains less than about 0.025% dsRNA.

In some embodiments, in vitro synthesized mRNA is purified at a scale of or greater than about 10 gram per batch, the purified mRNA composition contains less than about 0.1% dsRNA, and the purified mRNA has an integrity greater than about 85%. In some embodiments, in vitro synthesized mRNA is purified at a scale of or greater than about 10 gram per batch, the purified mRNA composition contains less than about 0.01% dsRNA, and the purified mRNA has an integrity greater than about 85%. In some embodiments, in vitro synthesized mRNA is purified at a scale of or greater than about 20 gram per batch, the purified mRNA composition contains less than about 0.025% dsRNA, and the purified mRNA has an integrity greater than about 85%.

In some embodiments, an mRNA purified according to a method provided herein is substantially free of enzyme reagents used in IVT including, but not limited to, RNA polymerase, DNAse I, pyrophosphatase, and/or RNAse inhibitor. In some embodiments, an mRNA purified according to the present invention contains less than about 5% (e.g., less than about 4%, 3%, 2%, or 1%) of enzyme reagents used in IVT. In some embodiments, a purified mRNA contains less than about 1% (e.g., less than about 0.9%, 0.8%, 0.7%, 0.6%, 0.4%, 0.3%, 0.2%, or 0.1%) of enzyme reagents used in IVT. In some embodiments, a purified mRNA contains undetectable enzyme reagents used in IVT as determined by, e.g., silver stain, gel electrophoresis, HPLC, ultra-performance liquid chromatography (UPLC), and/or CE, ethidium bromide and/or Coomassie staining.

In various embodiments, an mRNA purified according to a method provided herein maintains high degree of integrity. As used herein, the term "mRNA integrity" generally refers to the quality of mRNA after purification. mRNA integrity may be determined using methods well known in the art, for example, by RNA agarose gel electrophoresis. In some embodiments, mRNA integrity refers to the percentage of mRNA that is not degraded after a purification process. In some embodiments, mRNA integrity may be determined by banding patterns of RNA agarose gel electrophoresis. In some embodiments, a purified mRNA of the present invention shows little or no banding compared to reference band of RNA agarose gel electrophoresis. In some embodiments, a purified mRNA of the present invention has an integrity greater than about 60%, 70%, 80%, 90%, or 95% (e.g., greater than about 96%, 97%, 98%, 99% or more). In some embodiments, a purified mRNA of the present invention has an integrity greater than 98%. In some embodiments, a purified mRNA of the present invention has an integrity greater than 99%. In some embodiments, a purified mRNA of the present invention has an integrity of approximately 100%.

In some embodiments, in vitro synthesized mRNA is purified at a scale of or greater than about 10 gram per batch, and the purified mRNA has an integrity greater than about 80% (e.g., at least about 85%). In some embodiments, in vitro synthesized mRNA is purified at a scale of or greater than about 20 gram per batch, and the purified mRNA has an integrity greater than about 80% (e.g., at least about 85%).

In some embodiments, the purified mRNA is assessed for one or more of the following characteristics: appearance, identity, quantity, concentration, presence of impurities, microbiological assessment, pH level and activity. In some embodiments, acceptable appearance includes a clear, colorless solution, essentially free of visible particulates. In some embodiments, the identity of the mRNA is assessed by sequencing methods. In some embodiments, the concentration is assessed by a suitable method, such as UV spectrophotometry. In some embodiments, a suitable concentration is between about 90% and 110% nominal (e.g., 0.9-1.1 mg/mL).

In some embodiments, assessing the purity of the mRNA includes assessment of mRNA integrity and assessment of residual plasmid DNA. In some embodiments, acceptable levels of mRNA integrity are assessed by agarose gel electrophoresis. The gels are analyzed to determine whether the banding pattern and apparent nucleotide length is consistent with an analytical reference standard. Additional methods to assess RNA integrity include, for example, assessment of the purified mRNA using capillary gel electrophoresis (CGE). In some embodiments, acceptable purity of the purified mRNA as determined by CGE is that the purified mRNA composition has no greater than about 40% long abortive/degraded species.

In some embodiments, microbiological tests are performed on the purified mRNA, which include, for example, assessment of bacterial endotoxins. In some embodiments, bacterial endotoxins are <0.5 EU/mL, <0.4 EU/mL, <0.3 EU/mL, <0.2 EU/mL or <0.1 EU/mL. Accordingly, in some embodiments, bacterial endotoxins in the purified mRNA are <0.5 EU/mL. In some embodiments, bacterial endotoxins in the purified mRNA are <0.4 EU/mL. In some embodiments, bacterial endotoxins in the purified mRNA are <0.3 EU/mL. In some embodiments, bacterial endotoxins in the purified mRNA are <0.2 EU/mL. In some embodiments, bacterial endotoxins in the purified mRNA are <0.1 EU/mL.

In some embodiments, the pH of the purified mRNA is assessed. In some embodiments, acceptable pH of the purified mRNA is between 5 and 8. Accordingly, in some embodiments, the purified mRNA has a pH of about 5. In some embodiments, the purified mRNA has a pH of about 6. In some embodiments, the purified mRNA has a pH of about 7. In some embodiments, the purified mRNA has a pH of about 7. In some embodiments, the purified mRNA has a pH of about 8.

In some embodiments, the translational fidelity of the purified mRNA is assessed. Translational fidelity can be assessed by various methods and include, for example, transfection and Western blot analysis. Acceptable characteristics of the purified mRNA includes banding pattern on a Western blot that migrates at a similar molecular weight as a reference standard. In some embodiments, the purified mRNA is assessed for conductance. In some embodiments, acceptable characteristics of the purified mRNA include a conductance of between about 50% and 150% of a reference standard.

The purified mRNA is also assessed for Cap percentage and for poly(A) tail length. In some embodiments, an acceptable Cap percentage includes Cap1, % Area: NLT90. In some embodiments, an acceptable poly(A) tail length is about 100-1500 nucleotides (e.g., 100, 150, 200, 250, 300, 350, 400, 450, 500, 550, 600, 650, 700, 750, 800, 850, 900, 950, 1000, 1100, 1200, 1300, 1400, or 1500 nucleotides). Accordingly, in some embodiments an acceptable poly(A) tail length is about 100 nucleotides. In some embodiments, an acceptable poly(A) tail length is about 200 nucleotides. In some embodiments, an acceptable poly(A) tail length is about 250 nucleotides. In some embodiments, an acceptable poly(A) tail length is about 300 nucleotides. In some embodiments, an acceptable poly(A) tail length is about 350 nucleotides. In some embodiments, an acceptable poly(A) tail length is about 400 nucleotides. In some embodiments, an acceptable poly(A) tail length is about 450 nucleotides. In some embodiments, an acceptable poly(A) tail length is about 500 nucleotides. In some embodiments, an acceptable poly(A) tail length is about 550 nucleotides. In some embodiments, an acceptable poly(A) tail length is about 600 nucleotides. In some embodiments, an acceptable poly(A) tail length is about 650 nucleotides. In some embodiments, an acceptable poly(A) tail length is about 700 nucleotides. In some embodiments, an acceptable poly(A) tail length is about 750 nucleotides. In some embodiments, an acceptable poly(A) tail length is about 800 nucleotides. In some embodiments, an acceptable poly(A) tail length is about 850 nucleotides. In some embodiments, an acceptable poly(A) tail length is about 900 nucleotides. In some embodiments, an acceptable poly(A) tail length is about 950 nucleotides. In some embodiments, an acceptable poly(A) tail length is about 1000 nucleotides. In some embodiments, an acceptable poly(A) tail length is about 1100 nucleotides. In some embodiments, an acceptable poly(A) tail length is about 1200 nucleotides. In some embodiments, an acceptable poly(A) tail length is about 1300 nucleotides. In some embodiments, an acceptable poly(A) tail length is about 1400 nucleotides. In some embodiments, an acceptable poly(A) tail length is about 1500 nucleotides.

In some embodiments, in vitro synthesized mRNA is purified at a scale of or greater than about 10 gram per batch, and the purified mRNA has a cap percentage of at least about 90%. In some embodiments, in vitro synthesized mRNA is purified at a scale of or greater than about 20 gram per batch, and the purified mRNA has a cap percentage of at least about 90%.

In some embodiments, in vitro synthesized mRNA is purified at a scale of or greater than about 10 gram per batch, and has a poly(A) tail length of at least about 100 nucleotides. In some embodiments, in vitro synthesized mRNA is purified at a scale of or greater than about 20 gram per batch, and has a poly(A) tail length of at least about 100 nucleotides.

Various methods of detecting and quantifying mRNA purity are known in the art. For example, such methods include, blotting, capillary electrophoresis, chromatography, fluorescence, gel electrophoresis, HPLC, silver stain, spectroscopy, ultraviolet (UV), or UPLC, or a combination thereof. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

The preparation comprising mRNA provided in step (a) is an impure preparation (i.e., it comprises impurities). As used herein, the term "impurities" refers to substances inside a confined amount of liquid, gas, or solid, which differ from the chemical composition of the target material or compound. Impurities are also referred to as contaminants. The mRNA purification strategy described herein is capable of removing numerous impurities associated with IVT-produced mRNA, such as IVT enzymes (i.e., the RNA polymerase), free NTPs, buffer components (i.e., salts), mRNA fragments (e.g., prematurely aborted sequences), and untailed mRNA. The mRNA purification strategy described herein is also capable of removing nucleic acid contaminants, such as double-stranded RNA and residual plasmid DNA. The mRNA purification strategy described herein can therefore be used to provide a purified mRNA preparation that is suitable for therapeutic use.

As used herein, the term "affinity chromatography" or "affinity purification" refers to a separation method based on a specific binding interaction between a ligand immobilized or coupled to a solid support and its binding partner. When a complex mixture is passed through a column, molecules with specific binding affinity for the ligand are bound. After other sample components are washed away, the bound molecules are removed from the solid support, resulting in their purification from the original mixture. Each specific affinity system requires its own set of conditions known to those skilled in the art.

As used herein, the term "oligo dT" refers to a single-stranded sequence of deoxythymidine (dT). Oligo dT binds to the poly(A) tail of an mRNA molecule, and may be used as a method for purifying mRNA. The oligo dT can be of any length suitable to hybridize to a poly(A) tail, e.g., a 12 to 50-mer. Multiple types of oligo dT ligands are known in the art and commercially available. For example, oligo(dT) 25 is a homogenous mixture of deoxythymidines, while oligo (dT)$_{12-18}$ is a mixture of 12-mer to 18-mer deoxythymidines.

In some embodiments, the method of purifying mRNA does not comprise a step of applying the preparation to a primary amino solid phase. The term "primary amino solid phase" refers to a solid phase suitable for performing chromatography that dominantly or exclusively bears primary amino ligands on its surface(s).

I. Proteinase Treatment

In some embodiments, one or more proteinases may be used to enzymatically digest proteins used in the in vitro transcription, DNase treatment, capping, and/or tailing reactions and facilitate purification of the mRNA. In some embodiments, the proteinase comprises a serine protease (e.g., proteinase K, chymotrypsin and chymotrypsin-like serine protease, trypsin and trypsin-like serine protease, elastase and elastase-like serine protease, subtilisin and subtilisin-like serine protease), a cysteine protease, a threonine protease, an aspartic protease, a glutamic protease, a metalloprotease, and an asparagine peptide lyase.

In some embodiments, the proteinase is a serine protease. In some embodiments, the proteinase is proteinase K. Proteinase K is a serine protease that exhibits a very broad cleavage specificity, and it cleaves peptide bonds adjacent to the carboxylic group of aliphatic and aromatic amino acids. By subjecting a preparation comprising mRNA to an enzymatic digestion with a proteinase, such as serine protease, one can advantageously achieve degradation and inactivation of enzymes. Proteinase treatment greatly facilitates downstream mRNA purification. Shorter peptide fragments of the IVT enzymes are easier to purify away using filtration (i.e., TFF) and/or chromatography-based purification (e.g., affinity chromatography, such as oligo dT chromatography). In some embodiments, the serine proteinase is a proteinase K from *Engyodontium album*. In some embodiments, the proteinase K is a recombinant protein. In some embodiments, the proteinase K is thermolabile. In some embodiments, the proteinase K is selected from among the variants described in U.S. Pat. No. 10,633,644B1.

In some embodiments, a preparation comprising in vitro synthesized mRNA is subjected to an enzymatic digestion with a proteinase, such that an mRNA-proteinase mixture is obtained. In some embodiments, the preparation comprising in vitro synthesized mRNA is incubated with the proteinase at about 25° C. to about 40° C. for at least 30 minutes. In some embodiments, the preparation comprising in vitro synthesized mRNA is incubated with the proteinase at about 25° C., 26° C., 27° C., 28° C., 29° C., 30° C., 31° C., 32° C., 33° C., 34° C., 36° C., 37° C., 38° C., 39° C., or 40° C. for at least 30 minutes. In some embodiments, the preparation comprising in vitro synthesized mRNA is incubated with the proteinase at about 37° C. for at least about 30 minutes. In some embodiments, the preparation comprising in vitro synthesized mRNA is incubated with the proteinase at about 25° C. to about 40° C. for about 30 minutes, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, or about 240 minutes. In some embodiments, the preparation comprising in vitro synthesized mRNA is incubated with the proteinase at about 37° C. for about 30 minutes, about 45 minutes, about 60 minutes, about 75 minutes, about 90 minutes, about 105 minutes, about 120 minutes, about 135 minutes, about 150 minutes, about 165 minutes, about 180 minutes, about 195 minutes, about 210 minutes, about 225 minutes, or about 240 minutes.

In some embodiments, the proteinase is at a concentration of at least about 0.02 U/mg RNA. In some embodiments, the proteinase is at a concentration of at least about 0.04, 0.05, 0.06, 0.07, 0.08, 0.09, 0.1, 0.2, 0.3, 0.4, or 0.5 U/mg RNA. In some embodiments, the proteinase is at a concentration of 0.02-0.6 U/mg RNA. In some embodiments, the proteinase is at a concentration of 0.02-0.03 U/mg RNA. In some embodiments, the proteinase is at a concentration of about 0.5-0.6 U/mg RNA. In some embodiments, the proteinase is at a concentration of about 0.55 U/mg RNA. In some embodiments, the preparation comprising in vitro synthesized mRNA is incubated with the proteinase at a concentration of 0.02-0.6 U/mg RNA at about 37° C. for at least about 30 minutes.

In some embodiments, the mRNA-proteinase mixture (i.e., the preparation comprising in vitro synthesized mRNA and the proteinase) is stirred. The term "stirred" as used herein means any action which is suitable to mix a mixture, e.g., composed of the preparation comprising in vitro synthesized mRNA and a proteinase. Exemplary devices to achieve stirring are known to the skilled person and include a shaker, a mixer (e.g., a vortex mixer or a static mixer), a magnetic stirrer (including a stir bar), and a stirring rod, which are available in different sizes depending on the volume of the mixture to be mixed. Stirring can be performed for a time sufficient to achieve a thorough mixing. Stirring enhances the overall efficacy of the proteinase treatment, particularly for large-scale mRNA purification of at least about 1 gram.

In some embodiments, the mRNA purification described herein comprises one step of enzymatic digestion with a proteinase, followed by an affinity chromatography step (e.g., oligo dT). Additional steps may be present between the step of enzymatic digestion with a proteinase and the affinity chromatography step, such as a TFF step, a capping step, and/or tailing step.

In one aspect, a method of purifying mRNA is provided herein comprising: (a) subjecting a preparation comprising in vitro synthesized mRNA to an enzymatic digestion with a proteinase; (b) subjecting the preparation obtained from step (a) to a step of TFF; (c) subjecting the preparation obtained from step (b) to an oligo dT affinity chromatography; and (d) subjecting the preparation obtained from step (c) to a step of TFF.

In other embodiments, the mRNA purification described herein comprises a first step of enzymatic digestion with a proteinase, followed by a second step of enzymatic digestion with a proteinase. At least one additional step occurs between the first and second steps of enzymatic digestion with a proteinase, such as a TFF step, a capping step, a tailing step, and/or a frontal filtration step, as provided herein. In some embodiments, the first step of enzymatic digestion is followed by a step of TFF, and then a step of capping and/or tailing. In some embodiments, the first step of enzymatic digestion is followed by a step of TFF, then a step of capping and/or tailing and then a step of frontal filtration. In some embodiments, where a first and second step of enzymatic digestion with a proteinase is performed, no affinity chromatography step is performed.

In one aspect, a method of purifying mRNA is provided herein, comprising: (a) subjecting a preparation comprising in vitro synthesized mRNA to a first enzymatic digestion with a proteinase; (b) subjecting the preparation obtained from step (a) to a second enzymatic digestion with a proteinase; and (c) subjecting the preparation obtained from step (b) to a step of TFF.

In another aspect, a method of purifying mRNA is provided herein, comprising: (a) subjecting a preparation comprising in vitro synthesized mRNA to an enzymatic digestion with a proteinase; (b) subjecting the preparation obtained from step (a) to step of TFF; (c) subjecting the preparation obtained from step (b) to an enzymatic digestion with a proteinase; and (d) subjecting the preparation obtained from step (c) to a step of TFF.

In another aspect, the disclosure provides a method of purifying mRNA, comprising: (a) subjecting a preparation comprising in vitro synthesized mRNA to a first proteinase incubation step, thereby producing a first mRNA-proteinase mixture; (b) subjecting the first mRNA-proteinase mixture to a first step of TFF, thereby producing a first filtered mRNA mixture; (c) subjecting the first filtered mRNA mixture to a second proteinase incubation step, thereby producing a second mRNA-proteinase mixture; and (d) subjecting the second mRNA-proteinase mixture to a second step of TFF, thereby producing a purified mRNA.

In any of the methods provided herein, no precipitation step is performed (e.g., the preparation comprising in vitro synthesized mRNA is not subjected to an ethanol-mediated precipitation step).

A particular advantage provided by the present invention is the ability to purify mRNA, in particular, mRNA synthesized in vitro, at a large or commercial scale. For example, in some embodiments in vitro synthesized mRNA is purified at a scale of or greater than about 100 milligram, 1 gram, 10 gram, 50 gram, 100 gram or more per batch.

In one particular embodiment, in vitro synthesized mRNA is purified at a scale of 10 gram per batch. In one particular embodiment, in vitro synthesized mRNA is purified at a scale of 20 gram per batch. In one particular embodiment, in vitro synthesized mRNA is purified at a scale of 25 gram per batch. In one particular embodiment, in vitro synthesized mRNA is purified at a scale of 50 gram per batch. In another particular embodiment, in vitro synthesized mRNA is purified at a scale of 100 gram per batch or more.

In any of the methods provided herein, at least about 0.5 grams of mRNA is purified. In some embodiments, about 0.5 grams to about 100 grams of mRNA is purified. In some embodiments, about 0.5 grams, about 1 gram, about 5 grams, about 10 grams, about 15 grams, about 20 grams, about 25 grams, about 30 grams, about 35 grams, about 40 grams, about 45 grams, about 50 grams, about 55 grams, about 60 grams, about 65 grams, about 70 grams, about 75 grams, about 80 grams, about 85 grams, about 90 grams, about 95 grams, or about 100 grams of mRNA is purified. In some embodiments, at least 0.5 grams, at least 1 gram, at least 5 grams, at least 10 grams, at least 15 grams, at least 20 grams, at least 25 grams, at least 30 grams, at least 35 grams, at least 40 grams, at least 45 grams, at least 50 grams, at least 55 grams, at least 60 grams, at least 65 grams, at least 70 grams, at least 75 grams, at least 80 grams, at least 85 grams, at least 90 grams, at least 95 grams, or at least 100 grams of mRNA is purified.

In further embodiments, the serine protease is inactivated after incubation with the preparation comprising in vitro transcribed mRNA. In some embodiments, the serine protease is inactivated with heating. In some embodiments, the serine protease is inactivated by heating the preparation to at least 55° C. In some embodiments, the serine protease is inactivated with a chelating agent, such as EDTA. In some embodiments, the serine protease is inactivated with a serine protease inhibitor, such as phenylmethylsulfonyl fluoride (PMSF). In some embodiments, the serine protease is inactivated with a reducing agent. Non-limiting examples of the reducing agents include dithiothreitol (DTT) and Tris-2-carboxyethylphosphine hydrochloride (TCEP). In certain embodiments, the DTT is added to a concentration of at least about 20 mM. In certain embodiments, the DTT is added to a concentration of about 20 mM, about 25 mM, about 30 mM, about 35 mM, about 40 mM, about 45 mM, about 50 mM, about 55 mM, about 60 mM, about 65 mM, about 70 mM, about mM, about 80 mM, about 85 mM, about 90 mM, about 95 mM, or about 100 mM.

II. Tangential Flow Filtration (TFF)

Tangential flow filtration (TFF), also referred to as cross-flow filtration, is a type of filtration wherein the material to be filtered is passed tangentially across a filter rather than through it. In TFF, undesired permeate passes through the filter, while the desired retentate (e.g., mRNA) passes along the filter and is captured or retained on the filter or membrane downstream. In contrast, in frontal filtration, the flow direction is perpendicular to the filter surface, as the material to be filtered is passed through the filter.

In an embodiment of the mRNA purification methods described herein, an mRNA-containing sample (e.g., a preparation comprising in vitro synthesized mRNA or an mRNA-proteinase mixture) is subjected to at least one TFF step (i.e., a first TFF step). In some embodiments, the mRNA-containing sample is subjected to a second TFF step.

In some embodiments, the mRNA-proteinase mixture is subjected to at least a first TFF step prior to an oligo dT affinity chromatography step. In some embodiments, the mRNA-proteinase mixture is subjected to at least a first TFF step after a first step of enzymatic digestion with a proteinase and prior to a second step of enzymatic digestion with a proteinase.

In an embodiment, a TFF step comprises about a 50 kDa to about a 300 kDa filter. In some embodiments, the TFF step comprises about a 50 kDa filter, a 60 kDa filter, a 70 kDa filter, an 80 kDa filter, a 90 kDa filter, a 100 kDa filter, a 110 kDa filter, a 120 kDa filter, a 130 kDa filter, a 140 kDa filter, a 150 kDa filter, a 160 kDa filter, a 170 kDa filter, a 180 kDa filter, a 190 kDa filter, a 200 kDa filter, a 210 kDa filter, a 220 kDa filter, a 230 kDa filter, a 240 kDa filter, a 250 kDa filter, a 260 kDa filter, a 270 kDa filter, a 280 kDa filter, a 290 kDa filter, or a 300 kDa filter. In some embodiments, the TFF step comprises about a 100 kDa to about a 300 kDa filter. In some embodiments, the TFF step comprises about a 50 kDa to about a 100 kDa filter. The kDa filter size refers to molecular weight cut-off (MWCO).

A suitable membrane for TFF may be made of any material. Suitable membrane materials include, but are not limited to, polyethersulfone (PES) (not modified), modified polyethersulfone (mPES; such as an mPES hollow fiber membrane), polyvinylidene fluoride (PVDF), cellulose acetate, nitrocellulose, mixed cellulose esters (MCE), ultra-high molecular weight polyethylene (UPE), polyfluorotetraethylene (PTFE), nylon, polysulfone, polyether sulfone, polyacrilonitrile, polypropylene, polyvinyl chloride, and any combination thereof. In one embodiment, the membrane is cellulose. In one embodiment, the membrane is a polyethersulfone (mPES) hollow fiber membrane.

A suitable membrane for the present invention may have various surface area. In some embodiments, a suitable membrane has a sufficiently large surface area to facilitate large scale production of mRNA. For example, a suitable membrane may have a surface area of or greater than about 1,500 cm$^2$, 2,000 cm$^2$, 2,500 cm$^2$, 3,000 cm$^2$, 3,500 cm$^2$, 4,000 cm², 4,500 cm², 5,000 cm², 7,500 cm², 10,000 cm², 5 m², 10 m², 12 m², 15 m², 20 m², 24 m², 25 m², 30 m², or 50 m².

In some embodiments, the mRNA-proteinase mixture is further subjected to a first TFF step prior to an oligo dT affinity chromatography step, wherein the TFF step comprises about a 100 kDa to about a 300 kDa filter.

In some embodiments, the mRNA-proteinase mixture is concentrated with the at least first TFF step. In some embodiments, the mRNA-proteinase mixture is diafiltrated with the at least first TFF step. In one embodiment, the mRNA-proteinase mixture is concentrated prior to diafiltration, thereby reducing the volume required for diafiltration.

In some embodiments, the mRNA-proteinase mixture is concentrated to at least about 5 mg/mL. In some embodiments, the mRNA-proteinase mixture is concentrated to at least about 10 mg/mL. In some embodiments, the mRNA-proteinase mixture is concentrated to about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20 mg/mL. In some embodiments, the mRNA-proteinase mixture is concentrated to about 10-12 mg/mL. In some embodiments, the mRNA-proteinase mixture is concentrated to no more than about 12 mg/mL.

In some embodiments, mRNA comprised in the preparation obtained from an oligo-dT affinity chromatography (i.e., an affinity purified mRNA) is subjected to a TFF step (e.g., a second TFF step). In some embodiments, a preparation that has been subjected to two separate steps of enzymatic digestion with a proteinase is further subjected to a TFF step (e.g., a second TFF step).

In some embodiments, the second TFF step comprises about a 50 kDa to about a 300 kDa filter. some embodiments, the second TFF step comprises about a 50 kDa to about a 100 kDa filter.

In some embodiments, the affinity purified mRNA is concentrated with the TFF step. In some embodiments, the affinity purified mRNA is diafiltrated with the TFF step. In some embodiments, the affinity purified mRNA is concentrated prior to diafiltration, as this advantageously reduces the volume required for diafiltration.

In some embodiments, the affinity purified mRNA is concentrated to at least about 0.5 mg/mL. In some embodiments, the affinity purified mRNA is concentrated to at least about 1 mg/mL. In some embodiments, the affinity purified mRNA is concentrated to at least about 2 mg/mL. In some embodiments, the affinity purified mRNA is concentrated to at least about 5 mg/mL.

In some embodiments, the affinity purified mRNA is concentrated to about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, or about 10 mg/mL.

In some embodiments, the affinity purified mRNA is diluted after diafiltration to less than about 2 mg/mL. In some embodiments, the affinity purified mRNA is diluted after diafiltration to less than about 1 mg/mL. In some embodiments, the affinity purified mRNA is diluted after diafiltration to less than about 0.5 mg/mL.

At least three process variables are important in a typical TFF process: the transmembrane pressure (TMP), feed rate, and flow rate of the permeate. The TMP is the force that drives fluid through the filter, carrying with it permeable molecules. In some embodiments, the TMP is between 1 and 30 pounds per square inch (psi), inclusive. In some embodiments, the TMP is from about 5 to about 15 psi. In some embodiments, the TMP is from about 7 to about 9 psi. In some embodiments, the TMP is about 1 psi, about 2 psi, about 3 psi, about 4 psi, about 5 psi, about 6 psi, about 7 psi, about 8 psi, about 9 psi, about 10 psi, about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, or about 30 psi. 1 psi is equivalent to about 0.07 bar. Accordingly, in some embodiments, the TMP is between about 0.07 and about 2.07 pounds bar, inclusive. In some embodiments, the TMP is from about 0.34 bar to about 1.03 psi. In some embodiments, the TMP is from about 0.48 bar to about 0.62 bar.

The feed rate (also known as the crossflow velocity) is the rate of the solution flow through the feed channel and across the filter. The feed rate determines the force that sweeps away molecules that may otherwise clog or foul the filter and thereby restrict filtrate flow. In some embodiments, the feed rate is between 1 and 1000 mL/minute. In some embodiments, the feed rate is between 50 and 800 mL/minute. In some embodiments, the feed rate is between 50 and 750 mL/minute. In some embodiments, the feed rate is between 50 and 300 mL/minute. In some embodiments, the feed rate is between 50 and 200 mL/minute. In some embodiments, the feed rate is between 75 and 200 mL/minute. In some embodiments, the feed rate is between 100 and 200 mL/minute. In some embodiments, the feed rate is between 125 and 175 mL/minute. In some embodiments, the feed rate is 130 mL/minute. In some embodiments, the feed rate is between 60 mL/min and 220 mL/min. In some embodiments, the feed rate is 60 mL/min or greater. In some embodiments, the feed rate is 100 mL/min or greater. In some embodiments, the feed rate is 150 mL/min or greater. In some embodiments, the feed rate is 200 mL/min or greater. In some embodiments, the feed rate is 220 mL/min or greater.

The flow rate of the permeate is the rate at which the permeate is removed from the system. For a constant feed rate, increasing permeate flow rates can increase the pressure across the filter, leading to enhanced filtration rates while also potentially increasing the risk of filter clogging or fouling. The principles, theory, and devices used for TFF are described in Michaels et al., "Tangential Flow Filtration" in Separations Technology, Pharmaceutical and Biotechnology Applications (W. P. Olson, ed., Interpharm Press, Inc., Buffalo Grove, 111. 1995). See also U.S. Pat. Nos. 5,256,294 and 5,490,937 for a description of high-performance tangential flow filtration (HP-TFF), which represents an improvement to TFF. In some embodiments, the flow rate is between 1 and 100 mL/minute. In some embodiments, the flow rate is between 10 and 100 mL/minute. In some embodiments, the flow rate is between 10 and 90 mL/minute. In some embodiments, the flow rate is between 10 and 80 mL/minute. In some embodiments, the flow rate is between 10 and 70 mL/minute. In some embodiments, the flow rate is between 10 and 60 mL/minute. In some embodiments, the flow rate is between 10 and 50 mL/minute. In some embodiments, the flow rate is between 10 and 40 mL/minute. In some embodiments, the flow rate is between 15 and 60 mL/minute. In some embodiments, the flow rate is between 20 and 40 mL/minute. In some embodiments, the flow rate is 10 mL/minute, 15 mL/minute, 20 mL/minute, 25 mL/minute, 30 mL/minute, 35 mL/minute, 40 mL/minute, 45 mL/minute, 50 mL/minute, 55 mL/minute, 60 mL/minute, 65 mL/minute, 70 mL/minute, 75 mL/minute, 80 mL/minute, 85 mL/minute, 90 mL/minute, 95 mL/minute, or 100 mL/minute.

Any combinations of various process variables described herein may be used. In some embodiments, the TFF is performed at a feed rate of approximately 100-200 mL/minute (e.g., approximately 100-180 mL/minute, 100-160 mL/minute, 100-140 mL/minute, 110-190 mL/minute, 110-170 mL/minute, or 110-150 mL/minute) and/or a flow rate of approximately 10-50 mL/minute (e.g., approximately 10-40 mL/minute, 10-30 mL/minute, 20-50 mL/minute, or 20-40 mL/minute). In some embodiments, the TFF is performed at a feed rate of approximately 100, 110, 120, 130, 140, 150, 160, 170, 180, 190, or 200 mL/minute and/or a flow rate of approximately 10, 20, 30, 40, or 50 mL/minute. In other embodiments, the TFF is performed at a feed rate of approximately 500, 750 mL/minute, 1, 2, 3, 4, or 5 L/min and/or a flow rate of approximately 100, 200, 250, 500, 750 mL/minute or 1 L/min.

In some embodiments, a filtration step is further performed after the step of affinity chromatography or after the second enzymatic digestion with a proteinase. In some embodiments, a sterilizing filtration, or frontal filtration, is performed. In some embodiments, filtration is performed on a filter having a pore size of 0.2 or 0.22 µm. In some embodiments, filtration is performed on a polyethersulfone (PES) filter.

In some embodiments, a step of frontal filtration is performed after capping. In some embodiments, a step of frontal filtration is performed after a step of TFF. In some embodiments, a step of frontal filtration is performed after capping and before oligo dT affinity chromatography. In some embodiments, a step of frontal filtration is performed after oligo dT affinity chromatography. In some embodiments, a step of frontal filtration is performed after a second step of TFF. In some embodiments, frontal filtration is performed on a filter having a pore size of 0.2 or 0.22 µm. In some embodiments, frontal filtration uses a polyethersulfone (PES) filter.

III. Affinity Chromatography

In one embodiment, mRNA from the impure preparation is purified by oligo dT chromatography. Oligo dT is a single stranded sequence of deoxythymidine (dT) and may be used as in affinity chromatography to purify mRNA that comprises a stretch of poly(A)s, such as a poly(A) tail. In one embodiment, the oligo dT is a homogenous mixture of 12, 13, 14, 15, 16, 17, 18, 19, 20, 21, 22, 23, 24, 25, 26, 27, 28, 29, or 30-mer deoxythymidines, such as oligo(dT)$_{12}$, oligo (dT)$_{14}$, oligo(dT)$_{18}$, oligo(dT)$_{20}$, oligo(dT)$_{23}$, or oligo (dT)$_{25}$. In another embodiment, the oligo dT is a mixture of two or more oligo(dT) ligands of different lengths, such as oligo(dT)$_{12\text{-}18}$. Oligo dT may be immobilized on chromatography resin, or other types of solid support. In particular, oligo dT may be bound to a monolithic matrix, a membrane, or beads. Oligo dT may be bound to one of the following supports: borosilicate glass, agarose, sepharose, magnetic beads, polystyrene, polyacrylamide, membranes, silica, semiconductor materials, silicon, organic polymers, ceramic, glass, metal, plastic polycarbonate, polycarbonate, polyethylene, polyethyleneglycol terephthalate, polymethylmethacrylate, polypropylene, polyvinylacetate, polyvinylchloride, polyvinylpyrrolidinone, or soda-lime glass. In one embodiment, oligo dT is bound to cross-linked poly(styrene-divinylbenzene) (PSDVB). In one embodiment, oligo dT is bound to sepharose. In one embodiment, oligo dT is bound to agarose. In one embodiment, oligo dT is bound to cellulose. In one embodiment, oligo dT is bound to poly (glycidyl methacrylate-co-ethylene dimethacrylate).

In some embodiments, the oligo dT is attached to the solid support via a linker, such as a carbon linker, which is positioned between the oligo dT molecule and the solid support. Linkers can be included at a variety of positions within or on oligo dT and/or a support. Selection of the linker is within the capabilities of the skilled person. Suitable linkers include alkyl and aryl groups, including heteroalkyl and heteroaryl, and substituted derivatives of these. In some instances, linkers can be amino acid based and/or contain amide linkages. Examples of linkers are: amino derivatives, thiol derivatives, aldehyde derivatives, formyl derivatives, azide derivatives (click chemistry), biotin derivatives, alkyne derivatives, hydroxyl derivatives, activated hydroxyls or derivatives, carboxylate derivatives, activated carboxylate derivates, activated carbonates, activated esters, nhs ester (succinimidyl), nhs carbonate (succinimidyl), imidoester or derivated, cyanogen bromide derivatives, maleimide derivatives, haloacteyl derivatives, iodoacetamide/iodoacetyl derivatives, epoxide derivatives, streptavidin derivatives, tresyl derivatives, diene/conjugated diene derivatives (diels alder type reaction), alkene derivatives, substituted phosphate derivatives, bromohydrin/halohydrin, substituted disulfides, pyridyl-disulfide derivatives, aryl azides, acyl azides, azlactone, hydrazide derivatives, halobenzene derivatives, nucleoside derivatives, branching/multifunctional linkers, dendrimeric functionalities, and/or nucleoside derivatives; or any combination thereof. In one embodiment, the linker comprises an amide bond. Non-limiting examples of carbon linkers include linkers of the formula $C_x$, wherein X is any whole number between 5 and 50. In some embodiments, the carbon linker is $C_6$, $C_7$, $C_8$, $C_9$, $C_{10}$, $C_{11}$, $C_{12}$, $C_{13}$, $C_{14}$, or $C_{15}$. In some embodiments, the linker comprises 5'-hexylamine. In some embodiments, oligo dT is attached to the support via an amide linkage. In some embodiments, oligo dT containing a amino group, such as 5'-hexylamine, is conjugated to a N-hydroxysuccinimidyl (NHS) ester that is bound to a support.

In an embodiment, an oligo dT chromatography resin comprises the structure:
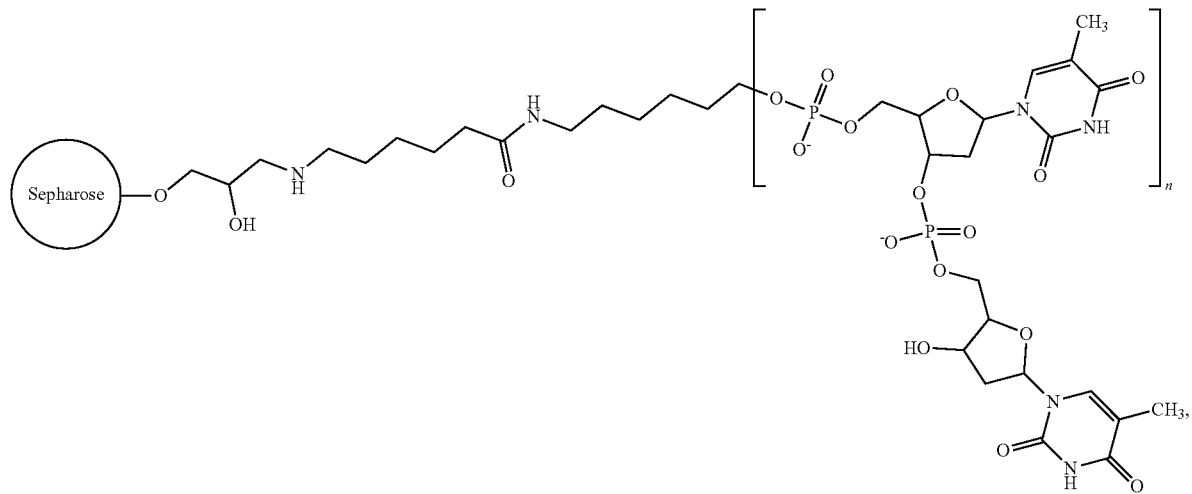
wherein n is an integer selected from the group consisting of 12, 13, 14, 15, 16, 17, 18, 19, 20, 21, 22, 23, 24, 25, 26, 27, 28, 29, or 30.
In an embodiment, an oligo dT chromatography resin comprises the structure:
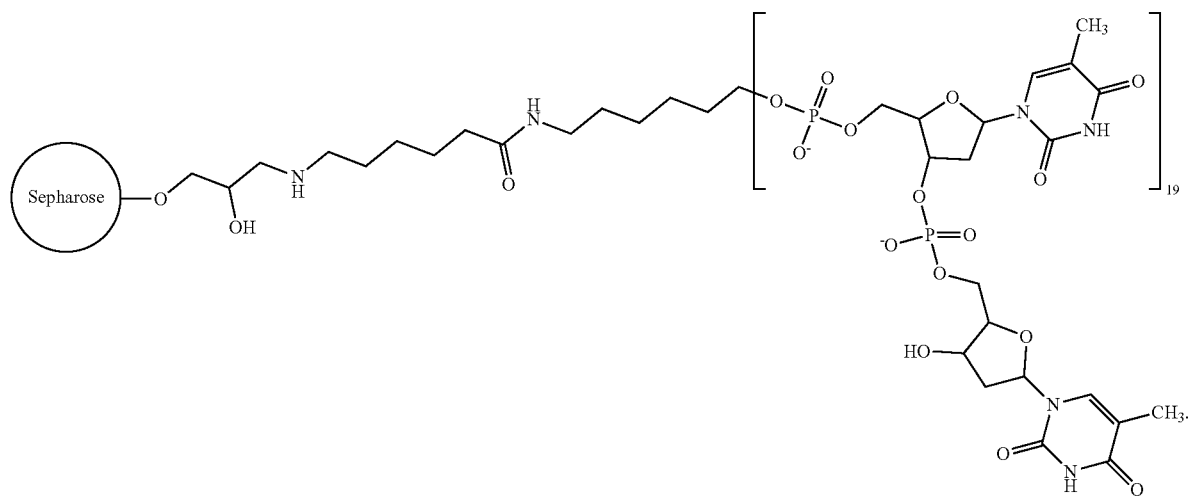

In an embodiment, an oligo dT chromatography resin comprises the structure:

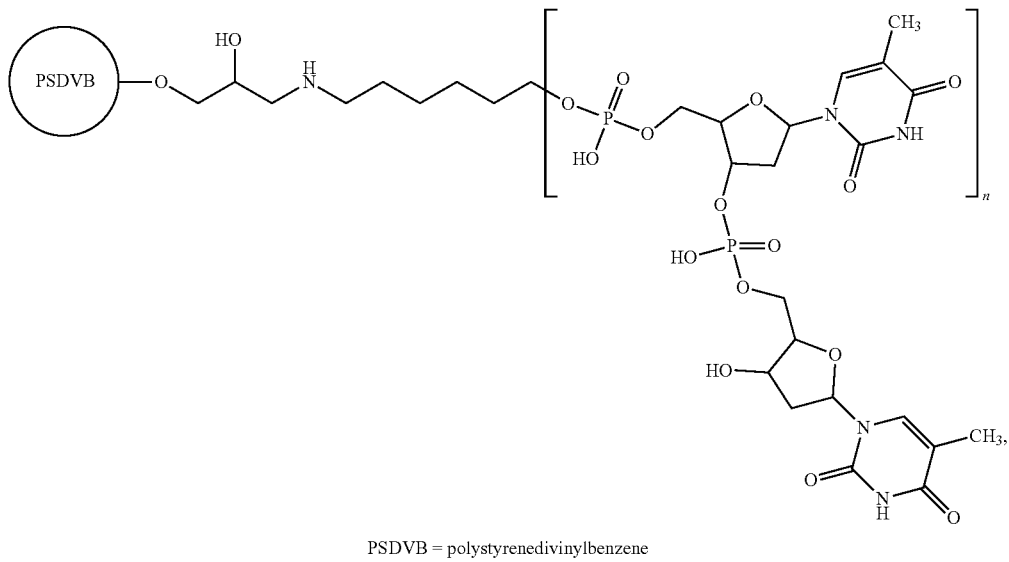

PSDVB = polystyrenedivinylbenzene wherein n is an integer selected from the group consisting of 12, 13, 14, 15, 16, 17, 18, 19, 20, 21, 22, 23, 24, 25, 26, 27, 28, 29, or 30. PSDVB is polystyrenedivinylbenzene.

In an embodiment, an oligo dT chromatography resin comprises the structure:

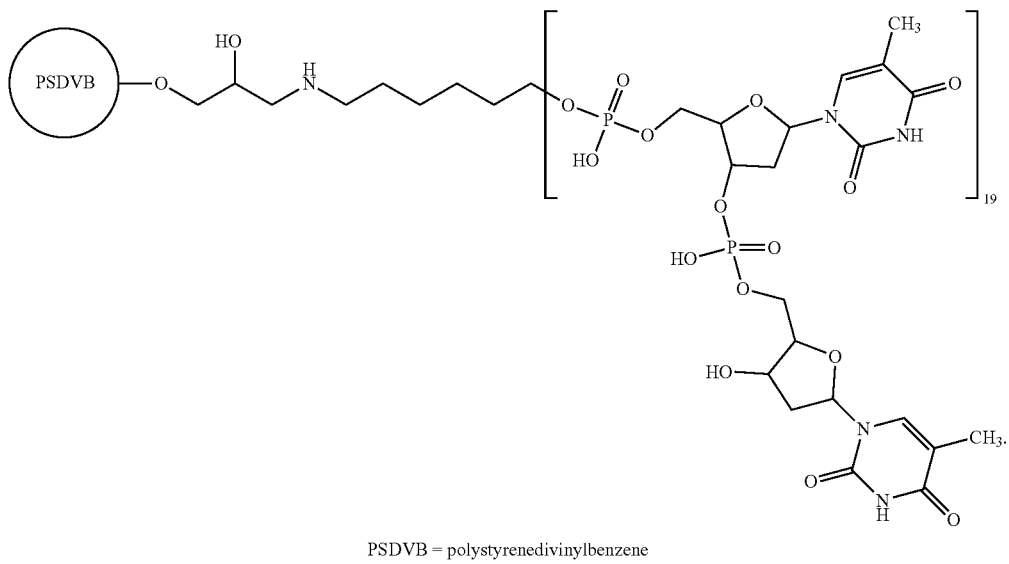

PSDVB = polystyrenedivinylbenzene

In an embodiment, the oligo dT affinity purification comprises an oligo(dT)$_{18}$ or oligo(dT)$_{25}$ chromatography resin. The mechanism of purification involves hybridization of the poly(A) tail of the mRNA to the oligo dT. Contaminant impurities in the preparation, such as proteins, unreacted nucleotides, plasmid DNA, CAP analogues, partial transcripts, dsRNA side products and enzymes, lack the poly(A) moiety and do not bind.

A sample loading buffer can be used for loading the mRNA preparation onto the oligo dT substrate (oligo dT immobilized on chromatography resin, or another type of solid support). Oligo dT affinity purification is typically performed with a salt concentration of up to around 250 mM in the sample loading buffer. Some salt is required in the loading buffer because under low conductivity conditions mutual electrostatic repulsion between the oligo dT substrate and the mRNA backbone is strong enough to prevent formation of hydrogen bonds (as would be required for hybridization of the poly(A) tail of the mRNA to the oligo dT). Increasing the concentration of salt in the loading buffer has a theoretical benefit of suppressing non-specific binding of the oligo dT substrate by contaminants. However, high salt concentrations may lead to the precipitation of the mRNA product (particularly when the mRNA is present at a high concentration in the sample), which can interfere with the flow of the mRNA preparation over the oligo dT substrate. This is particularly problematic for large batch sizes of mRNA, as the mRNA will typically be present at high concentrations (e.g., greater than 0.5 mg/ml) in the oligo dT loading buffer when a large amount of mRNA (e.g., at least about 10 g, 20 g, or 100 g) is purified in a single batch.

The negative effects associated with having a high salt concentration in the oligo dT loading buffer can be mitigated by minimizing the time period during which the mRNA sample is exposed to high salt conditions. Accordingly, in some embodiments a salt (e.g., sodium chloride) is added to a preparation comprising at least about 0.5 mg/ml mRNA to a final salt concentration of 400 mM to about 1200 mM no more than about 2 hours (e.g., no more than about 1 hour) before the preparation is applied to the oligo dT substrate. In some embodiments, a salt (e.g., sodium chloride) is added to a preparation comprising about 0.5 mg/ml to about 2.0 mg/ml mRNA to a final salt concentration of about 600 mM to about 1000 mM no more than about 2 hours before the preparation is applied to the oligo dT substrate. For example, in some embodiments, a salt (e.g., sodium chloride) is added to a preparation comprising about 2.0 mg/ml mRNA to a final salt concentration of about 800 mM no more than about 2 hours before the preparation is applied to the oligo dT substrate.

Sodium chloride is commonly added to the oligo dT loading buffer to increase its ionic strength. The inventors found that addition of 800 mM sodium chloride to 20 g-scale batch of mRNA at a concentration of approximately 2.0 mg/ml was suitable for oligo dT purification for a particular mRNA preparation. However, addition of sodium chloride to a final concentration of 800 mM to a 1 g batch of a different mRNA prior to loading onto the oligo dT substrate was found to cause mRNA precipitation, which led to column clogging and a reduced yield of purified mRNA. The inventors found that where mRNA precipitation is observed following addition of sodium chloride to the oligo dT load buffer, this precipitation can be at least partially prevented by replacing sodium chloride with potassium chloride (see Example 11). Thus, where mRNA precipitation is observed, the use of potassium chloride in place of sodium chloride can allow high salt concentrations to be used in the oligo dT loading buffer (to suppress non-specific binding of contaminants) with high concentrations of mRNA (so that smaller buffer volumes can be used for the purification of large batches of mRNA, for a faster purification process), while reducing the negative effect of mRNA precipitation. This is a surprising finding, because sodium chloride and potassium chloride are both neutral salts that have similar properties.

Accordingly, in some embodiments the oligo dT affinity chromatography step comprises loading a preparation comprising at least about 0.5 mg/ml mRNA and at least about 500 mM potassium chloride onto the oligo dT substrate. For example, in some embodiments, the preparation comprises about 0.5 mg/ml to about 2.0 mg/ml mRNA (e.g., about 1.0 mg/ml). In some embodiments, the preparation comprises about 500 mM to about 1000 mM potassium chloride (e.g., about 600 mM to about 900 mM potassium chloride).

A wash step removes the unbound contaminants, and poly(A) mRNA can then be eluted from the resin utilizing a low ionic strength buffer or a competitively binding oligonucleotide solution.

In an embodiment, the preparation comprising in vitro synthesized mRNA is diluted prior to an oligo dT affinity chromatography. In some embodiments, the dilution occurs after a capping step. In some embodiment, the dilution is at least 2-fold. In some embodiments, the dilution is about 2-fold, about 3-fold, about 4-fold, or about 5-fold.

In some embodiments, the method comprises subjecting the mRNA preparation to one step of oligo dT affinity chromatography, and does not include any additional affinity chromatography steps.

IV. Messenger RNA Capping and Tailing

In one embodiment, the method of purifying mRNA described herein comprises a step of capping. In some embodiments, a step of poly(A) tailing reaction is also performed.

In some embodiments, the mRNA is incubated with one or more capping enzymes to produce a capped mRNA. Capping may be performed at any point in the purification process. In one embodiment, capping occurs concomitantly to IVT. In another embodiment, capping occurs after IVT. In one embodiment, capping occurs prior to step (a) of subjecting a preparation comprising in vitro synthesized mRNA to an enzymatic digestion with a proteinase. In one embodiment, capping is performed on purified in vitro transcribed mRNA. In one embodiment, capping is performed after a first step of enzymatic digestion with a proteinase. In one embodiment, capping is performed after a preparation comprising in vitro synthesized mRNA has been subjected to a step of TFF. In one embodiment, capping is performed after a preparation comprising in vitro synthesized mRNA has been subjected to an enzymatic digestion with a proteinase and a step of TFF. In one embodiment, capping occurs prior to a step of affinity chromatography. In one embodiment, capping occurs prior to step (b) of subjecting the preparation obtained from step (a) to an oligo dT affinity chromatography in the method provided herein. In one embodiment, when the method comprises two steps of enzymatic digestion with a proteinase, capping occurs prior to the second step of enzymatic digestion with a proteinase.

In some embodiments, the mRNA is incubated with 2'O-methyltransferase and guanylyltransferase. In some embodiments, the mRNA is incubated with an RNAse inhibitor. In some embodiments, the mRNA is incubated with GTP and S-adenosylmethionine. In some embodiments, the mRNA is incubated with 2'O-methyltransferase, guanylyltransferase, GTP, and S-adenosylmethionine. In some embodiments, the mRNA is incubated with 2'O-methyltransferase, guanylyltransferase, an RNAse inhibitor, GTP, and S-adenosylmethionine.

In some embodiments, capping is performed at about 25° C. to about 37° C. for at least about 30 minutes. In some embodiments, the mRNA is incubated with the one or more capping enzymes at about 25° C. to about 37° C. for at least about 60 minutes. In some embodiments, the mRNA is incubated with the one or more capping enzymes at about 25° C. to about 37° C. for at least about 90 minutes. In some embodiments, capping is performed at about 25° C. to about 37° C. for at least about 120 minutes.

In some embodiments, capping is performed while stirring the mRNA-containing mixture.

In some embodiments, the mRNA lacks a poly(A) tail after the initial IVT reaction with an RNA polymerase and must be tailed.

In some embodiments, the mRNA is incubated with a poly(A) polymerase to produce a poly(A) tailed mRNA. In some embodiments, the poly(A) polymerase is an *E. coli* poly(A) polymerase.

In some embodiments, the mRNA is co-incubated with one or more capping enzymes and a poly(A) polymerase to produce a capped and poly(A) tailed mRNA. In other embodiments, the mRNA is incubated with one or more capping enzymes, followed by incubating the mRNA with a poly(A) polymerase to produce a capped and poly(A) tailed mRNA.

In some embodiments, tailing is performed at about 25° C. to about 37° C. for at least about 30 minutes. In some embodiments, tailing is performed at about 25° C. to about 37° C. for at least about 60 minutes. In some embodiments, tailing is performed at about 25° C. to about 37° C. for at least about 90 minutes. In some embodiments, tailing is performed at about 25° C. to about 37° C. for at least about 120 minutes.

In some embodiments, a step of frontal filtration is performed after capping. In some embodiments, when tailing is performed concomitantly to or after capping, the step of frontal filtration is performed after capping and tailing.

In one aspect, a method for manufacturing mRNA is provided herein, the method comprising: synthesizing mRNA in vitro; and purifying the in vitro synthesized mRNA using a method described herein.

In some embodiments, manufacturing the mRNA comprises a method for large-scale production of full-length mRNA molecules. In some embodiments, manufacturing the mRNA comprises a method for producing a composition enriched for full-length mRNA molecules which are greater than 500 nucleotides in length In some embodiments, at least 81%, 82%, 83%, 84%, 85%, 86%, 87%, 88%, 89%, 90%, 91%, 92%, 93%, 94%, 95%, 96%, 97%, 98%, 99%, 99.01%, 99.05%, 99.1%, 99.2%, 99.3%, 99.4%, 99.5%, 99.6%, 99.7%, 99.8%, 99.9% of the purified mRNA molecules are full-length mRNA molecules. In some embodiments, a composition or a batch includes at least 200 mg, 300 mg, 400 mg, 500 mg, 600 mg, 700 mg, 800 mg, 900 mg, 1 g, 5 g, 10 g, 25 g, 50 g, 75 g, 100 g, or more mRNA.

In another aspect, a mRNA obtainable by a method described herein is provided.

In another aspect, a composition comprising a purified mRNA obtained by a method described herein is provided. In some embodiments, the composition further comprises at least one pharmaceutically acceptable excipient.

In another aspect, a method for treating a disease or disorder comprising administering to a subject in need thereof a purified mRNA or a composition comprising a purified mRNA obtained by a method described herein is provided.

In another aspect, a purified mRNA or a composition comprising a purified mRNA obtained by a method described herein for use in therapy is provided.

The present invention comprises the following embodiments.

Embodiment 1. A method of purifying mRNA, comprising: (a) subjecting a preparation comprising in vitro synthesized mRNA to an enzymatic digestion with a proteinase; and (b) subjecting the preparation obtained from step (a) to an oligo dT affinity chromatography.

Embodiment 2. The method according to embodiment 1, wherein the proteinase comprises a serine protease.

Embodiment 3. The method according to embodiment 1 or 2, wherein the preparation comprising in vitro synthesized mRNA is incubated with the proteinase at about 37° C. for at least 30 minutes.

Embodiment 4. The method according to any one of embodiments 1-3, wherein the mRNA-proteinase mixture is stirred.

Embodiment 5. The method according to any one of embodiments 1-4, wherein the proteinase is inactivated with a reducing agent, optionally wherein the reducing agent is DTT.

Embodiment 6. The method according to any one of embodiments 5, wherein the DTT is added to a concentration of at least about 20 mM.

Embodiment 7. The method according to any one of embodiments 1-6, wherein the preparation obtained from step (a) is subjected to a step of TFF prior to step (b).

Embodiment 8. The method according to embodiment 7, wherein the TFF uses about a 100 kDa to about a 300 kDa filter.

Embodiment 9. The method according to embodiment 7 or 8, wherein the mRNA comprised in the preparation obtained from step (a) is concentrated with the TFF.

Embodiment 10. The method according to embodiment 9, wherein the mRNA comprised in the preparation obtained from step (a) is concentrated to at least about 5 mg/mL.

Embodiment 11. The method of any one of embodiments 1-10, wherein sodium citrate is added to the preparation obtained from step (a).

Embodiment 12. The method of embodiment 11, wherein sodium citrate is added at a concentration of at least about 10 mM, optionally at least about 25 mM.

Embodiment 13. The method of embodiment 11, wherein sodium citrate is added at a concentration of about 25 mM.

Embodiment 14. The method of any one of embodiments 11-13, wherein the preparation is held at about 35° C. to about 37° C. for at least about 5 minutes following the addition of sodium citrate.

Embodiment 15. The method of any one of embodiments 1-10, wherein EDTA is added to the preparation obtained from step (a).

Embodiment 16. The method of embodiment 15, wherein EDTA is added at a concentration of at least about 10 mM, optionally at least about 25 mM.

Embodiment 17. The method of embodiment 15, wherein EDTA is added at a concentration of about 25 mM.

Embodiment 18. The method of any one of embodiments 15-17, wherein the preparation is held at about 35° C. to about 37° C. for at least about 5 minutes following the addition of EDTA.

Embodiment 19. The method according to any one of embodiments 1-18, wherein the preparation is subjected to a step of capping prior to step (b) to produce a capped mRNA.

Embodiment 20. The method according to embodiment 19, wherein the preparation is incubated with 2'O-methyltransferase and guanylyltransferase.

Embodiment 21. The method according to embodiment 19 or 20, wherein the preparation is incubated with an RNAse inhibitor.

Embodiment 22. The method according to any one of embodiments 19-21, wherein the preparation is incubated with GTP and S-adenosylmethionine.

Embodiment 23. The method according to any one of embodiments 19-22, wherein capping is performed at about 37° C. for at least 30 minutes, optionally with stirring.

Embodiment 24. The method according to any one of embodiments 1-23, wherein the preparation is subjected to a step of tailing with a poly(A) polymerase to produce a poly(A) tailed mRNA.

Embodiment 25. The method according to any one of embodiments 1-23, wherein the preparation is co-incubated with one or more capping enzymes and a poly(A) polymerase to produce a capped and poly(A) tailed mRNA.

Embodiment 26. The method according to any one of embodiments 1-23, wherein the preparation is incubated with one or more capping enzymes, followed by incubating the mRNA with a poly(A) polymerase to produce a capped and poly(A) tailed mRNA.

Embodiment 27. The method according to any one of embodiments 1-26, wherein the oligo dT affinity chromatography uses an oligo(dT)$_{25}$ chromatography resin.

Embodiment 28. The method according to any one of embodiments 1-27, wherein the preparation obtained from step (b) is subjected to a step of TFF.

Embodiment 29. The method according to embodiment 28, wherein the TFF uses about a 50 kDa to about a 300 kDa filter.

Embodiment 30. The method according to embodiments 28 or 29, wherein the mRNA comprised in the preparation obtained from step (b) is concentrated with the TFF step.

Embodiment 31. The method according to embodiment 30, wherein the mRNA comprised in the preparation obtained from step (b) is concentrated to at least about 2 mg/mL.

Embodiment 32. The method of any one of embodiments 19-31, wherein the preparation is subjected to a step of frontal filtration after the capping step.

Embodiment 33. The method of any one of embodiments 19-31, wherein the preparation is subjected to a step of frontal filtration after the capping step and prior to step (b).

Embodiment 34. The method of any one of embodiments 28-33, further comprising a step of frontal filtration after the step of TFF.

Embodiment 35. A method of purifying mRNA, comprising: (a) subjecting a preparation comprising in vitro synthesized mRNA to an enzymatic digestion with a proteinase; (b) subjecting the preparation obtained from step (a) to a step of TFF; (c) subjecting the preparation obtained from step (b) to an oligo dT affinity chromatography; and (d) subjecting the preparation obtained from step (c) to a step of TFF.

Embodiment 36. The method according to embodiment 35, wherein the preparation obtained from step (b) is incubated with one or more capping enzymes to produce a capped mRNA.

Embodiment 37. The method according to embodiment 35 or 36, wherein the preparation obtained from step (b) is incubated with a poly(A) polymerase to produce a poly(A) tailed mRNA.

Embodiment 38. The method according to any one of embodiments 35-37, wherein the preparation obtained from step (b) is co-incubated with one or more capping enzymes and a poly(A) polymerase to produce a capped and poly(A) tailed mRNA.

Embodiment 39. The method of any one of embodiments 35-38, wherein the preparation is subjected to a step of frontal filtration prior to step (c).

Embodiment 40. The method of any one of embodiments 36-38, wherein the preparation is subjected to a step of frontal filtration after capping and prior to step (c).

Embodiment 41. The method of any one of embodiments 35-40, further comprising a step of frontal filtration after step (d).

Embodiment 42. The method of any one of embodiments 32-34 and 39-41, wherein the frontal filtration comprises a 0.2 µm filter.

Embodiment 43. A method of purifying messenger RNA (mRNA), comprising: (a) subjecting a preparation comprising in vitro synthesized mRNA to an enzymatic digestion with a proteinase; (b) subjecting the preparation obtained from step (a) to a step of tangential flow filtration (TFF); (c) subjecting the preparation obtained from step (b) to a step of capping; (d) subjecting the preparation obtained from step (c) to a step of frontal filtration; (e) subjecting the preparation obtained from step (d) to an oligo dT affinity chromatography; and (f) subjecting the preparation obtained from step (e) to a step of TFF.

Embodiment 44. The method of embodiment 43, wherein the method further comprises a step of frontal filtration after step (f).

Embodiment 45. The method of embodiment 43 or 44, wherein the frontal filtration comprises a 0.2 µm filter.

Embodiment 46. The method of any one of embodiments 32-34, 39-42, and 43-45, wherein the frontal filtration reduces guanylyltransferase (GuaT) content.

Embodiment 47. The method according to any one of the previous embodiments, wherein the oligo dT affinity chromatography comprises addition of a salt to the preparation to a final concentration of about 400 mM to about 1200 mM no more than 2 hours before the preparation is applied to the oligo dT substrate.

Embodiment 48. The method of embodiment 47, wherein the salt is added to the preparation to a final concentration of about 500 mM to about 1000 mM.

Embodiment 49. The method of any one of embodiments 47-48, wherein the salt is added to the preparation to a final concentration of about 800 mM.

Embodiment 50. The method of any one of embodiments 47-49 wherein the preparation comprises at least about 0.5 mg/ml mRNA.

Embodiment 51. The method of embodiment 50, wherein the preparation comprises about 0.5 mg/ml to about 2.0 mg/ml mRNA.

Embodiment 52. The method of embodiment 51, wherein the preparation comprises about 1.0 mg/ml mRNA.

Embodiment 53. The method of any one of embodiments 47-52, wherein the salt is sodium chloride.

Embodiment 54. The method of any one of embodiments 47-52, wherein the salt is potassium chloride.

Embodiment 55. The method according to any one of embodiments 47-52, and 54, wherein the oligo dT affinity chromatography comprises loading a preparation comprising at least about 0.5 mg/ml mRNA and at least about 500 mM potassium chloride onto the oligo dT substrate.

Embodiment 56. The method of embodiment 55, wherein the preparation comprises about 500 mM to about 1000 mM potassium chloride.

Embodiment 57. The method of embodiment 56, wherein the preparation comprises about 600 mM to about 900 mM potassium chloride.

Embodiment 58. A method of purifying mRNA, comprising: (a) subjecting a preparation comprising in vitro synthesized mRNA to a first enzymatic digestion with a proteinase; (b) subjecting the preparation obtained from step (a) to a second enzymatic digestion with a proteinase; and (c) subjecting the preparation obtained from step (b) to a step of TFF.

Embodiment 59. The method according to embodiment 58, wherein the proteinase comprises a serine protease.

Embodiment 60. The method according to embodiment 58 or 59, wherein the first enzymatic digestion and/or the second enzymatic digestion occurs at about 37° C. for at least 30 minutes.

Embodiment 61. The method according to any one of embodiments 58-60, wherein the first enzymatic digestion and/or the second enzymatic digestion is stirred.

Embodiment 62. The method according to any one of embodiments 58-61, wherein the proteinase is inactivated with a reducing agent, optionally wherein the reducing agent is dithiothreitol (DTT).

Embodiment 63. The method according to embodiment 62, wherein the DTT is added to a concentration of at least about 20 mM.

Embodiment 64. The method according to any one of the previous embodiments, wherein no precipitation step is performed.

Embodiment 65. The method according to any one of the previous embodiments, wherein at least about 0.5 grams of mRNA is purified.

Embodiment 66. The method according to any one of the previous embodiments, wherein about 0.5 grams to about 100 grams of mRNA is purified.

Embodiment 67. The method according to any one of the previous embodiments, wherein the in vitro synthesized mRNA is purified at a scale of or greater than about 100 milligram, 1 gram, 10 gram, 20 gram, 50 gram, 100 gram or more per batch, optionally wherein the mRNA is purified at a scale of or greater than about 10 gram per batch.

Embodiment 68. The method according to any one of the previous embodiments, wherein the residual plasmid DNA in the purified mRNA is less than about 1 pg/mg.

Embodiment 69. The method according to embodiment 68, wherein the residual plasmid DNA in the purified mRNA is less than about 0.5 pg/mg.

Embodiment 70. The method according to embodiment 69, wherein the residual plasmid DNA in the purified mRNA is less than or equal to about 0.2 pg/mg.

Embodiment 71. The method according to any one of the previous embodiments, wherein the in vitro synthesized mRNA is purified at a scale of or greater than about 10 gram per batch, and the residual plasmid DNA in the purified mRNA is less than or equal to about 0.2 pg/mg.

The method according to embodiment 72, wherein the in vitro synthesized mRNA is purified at a scale of or greater than about 20 gram per batch, and the residual plasmid DNA in the purified mRNA is less than or equal to about 0.2 pg/mg.

Embodiment 73. The method according to any one of the previous embodiments, wherein the method removes more than about 80%, 85%, 90%, 95%, 96%, 97%, 98%, 99% or substantially all prematurely aborted RNA sequences.

Embodiment 74. The method according to any one of the previous embodiments, wherein the purified mRNA contains less than about 5% (e.g., less than about 4%, 3%, 2%, or 1%) of prematurely aborted RNA sequences.

Embodiment 75. The method according to embodiment 74, wherein the purified mRNA contains less than about 1% (e.g., less than about 0.9%, 0.8%, 0.7%, 0.6%, 0.5%, 0.3%, 0.2%, or 0.1%) of prematurely aborted RNA sequences.

Embodiment 76. The method according to any one of the previous embodiments, wherein the purified mRNA contains less than about 1% (e.g., less than about 0.5%, 0.2%, or 0.1%) of dsRNA.

Embodiment 77. The method according to embodiment 76, wherein the purified mRNA contains less than about 0.1% (e.g., less than about 0.050%, 0.030%, 0.025%, or of dsRNA.

Embodiment 78. The method according to any one of the previous embodiments, wherein the in vitro synthesized mRNA is purified at a scale of or greater than about 10 gram per batch, and the purified mRNA contains less than about 0.01% of dsRNA.

Embodiment 79. The method according to embodiment XX, wherein the in vitro synthesized mRNA is purified at a scale of or greater than about 20 gram per batch, and the purified mRNA contains less than about 0.025% of dsRNA.

Embodiment 80. The method according to any one of the previous embodiments, wherein the purified mRNA contains less than about 5% (e.g., less than about 4%, 3%, 2%, or 1%) of enzyme reagents used in in vitro synthesis.

Embodiment 81. The method according to embodiment 80, wherein the purified mRNA contains less than about 1% (e.g., less than about 0.9%, 0.8%, 0.7%, 0.6%, 0.5%, 0.3%, 0.2%, or 0.1%) of enzyme reagents used in in vitro synthesis.

Embodiment 82. The method according to any one of the previous embodiments, wherein the purified mRNA contains undetectable enzyme reagents used in in vitro synthesis as determined by, e.g., silver stain, gel electrophoresis, HPLC, ultra-performance liquid chromatography (UPLC), and/or CE, ethidium bromide and/or Coomassie staining.

Embodiment 83. The method according to any one of the previous embodiments, wherein the in vitro synthesized mRNA is purified at a scale of or greater than about 10 gram per batch, and the purified mRNA contains undetectable enzyme reagents used in in vitro synthesis as determined by silver stain.

Embodiment 84. The method according to embodiment 83, wherein the in vitro synthesized mRNA is purified at a scale of or greater than about 20 gram per batch, and the purified mRNA contains undetectable enzyme reagents used in in vitro synthesis as determined by silver stain.

Embodiment 85. The method according to any one of the previous embodiments, wherein the purified mRNA has an integrity greater than about 60%, 70%, 80%, 90%, or 95% (e.g., greater than about 96%, 97%, 98%, 99% or more).

Embodiment 86. The method according to any one of the previous embodiments, wherein the purified mRNA has an integrity greater than about 80%.

Embodiment 87. The method of according to embodiment 86, wherein the purified mRNA has an integrity greater than about 85%.

Embodiment 88. The method according to any one of the previous embodiments, wherein the in vitro synthesized mRNA is purified at a scale of or greater than about 10 gram per batch, and the purified mRNA has an integrity greater than about 80% (e.g., at least about 85%).

Embodiment 89. The method according to embodiment 88, wherein the in vitro synthesized mRNA is purified at a scale of or greater than about 20 gram per batch, and the purified mRNA has an integrity greater than about 80% (e.g., at least about 85%).

Embodiment 90. The method according to any one of the previous embodiments, wherein the method does not comprise a step of contacting the preparation with an RNase III.

Embodiment 91. The method according to any one of the previous embodiments, wherein the method does not comprise a step of applying the preparation to a primary amino solid phase.

Embodiment 92. The method according to any one of the previous embodiments, wherein the method does not include any additional affinity chromatography steps.

Embodiment 93. The method according to any one of the previous embodiments, wherein the method does not include any additional filtration steps.

Embodiment 94. The method according to any one of the previous embodiments, wherein the method does not include any additional purification steps.

Embodiment 95. The method according to any one of the previous embodiments, wherein the purified mRNA is suitable for therapeutic use.

Embodiment 96. A method for manufacturing mRNA comprising: synthesizing mRNA in vitro; and purifying the in vitro synthesized mRNA using a method according to any one of the previous embodiments.

Embodiment 97. A mRNA obtainable by a method according to any one of the previous embodiments.

EXAMPLES

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The methods described below were performed in a nuclease free environment where: a) all single use components (e.g., bottles, pipette tips, tubing, etc.), assemblies, and equipment were RNAse free via gamma irradiation treatment or decontamination by sodium hydroxide treatment with sufficient contact time and then rinsed with RNAse free water; b) buffers were prepared from powder or concentrated commercial solutions in sterile vessels and under biosafety laminar flow and were finally filtered on 0.22 μm vacuum filters; and c) surfaces were decontaminated with commercial RNAse, cleaning solution, and wipes.

Example 1: RNA Synthesis

IVT Reaction Conditions

For the following examples, mRNA was in vitro transcribed by standard methods. Briefly, for each gram of mRNA transcribed, a reaction containing linearized double-stranded DNA plasmid with an RNA polymerase-specific promoter, RNA polymerase (e.g., SP6 polymerase or T7 polymerase), RNase inhibitor, pyrophosphatase, NTPs, DTT, and a reaction buffer was prepared with RNase-free water then incubated at 37° C. for a specified time. The reaction was then quenched by the addition of DNase I and a DNase I buffer to facilitate digestion of the double-stranded DNA template in preparation for purification. 1 gram of in vitro transcribed mRNA was subjected to various purification methods.

Capping

Following synthesis of mRNA as described above, the in vitro transcribed mRNA was modified enzymatically by the addition of a 5' $N^7$-methylguanylate Cap 0 structure using guanylyl transferase and the addition of a methyl group at the 2' O position of the penultimate nucleotide resulting in a Cap 1 structure using 2'O-methyltransferase as described by Fechter, P. and Brownlee, G. G. "Recognition of mRNA cap structures by viral and cellular proteins" *J. Gen. Virology* 2005, 86, 1239-1249. Capping was performed immediately prior to the affinity chromatography step when performing the enzymatic/affinity method and immediately prior to the second step of enzymatic digestion with a proteinase when performing the full enzymatic method.

Tailing

Unless otherwise described, the IVT transcribed mRNA was tailed on its 3' end either by including a tail template in the linearized plasmid, which tails the mRNA as part of the IVT reaction, or in a subsequent enzymatic step. For tailing as part of the IVT reaction, incorporation of a poly(T) or similar tailing feature into the pDNA template is performed such that the poly(A) tail or similar appropriate tail is formed on the mRNA as part of the IVT process. Alternatively, a poly(A) tail can be added to the 3' end of the IVT-produced mRNA enzymatically following the IVT reaction, e.g., using poly(A) polymerase.

Example 2: Ethanol-Based Purification Method (Comparative Example)

Purification of the IVT reaction using ethanol-based precipitation was performed using the method summarized in Table 8 of WO 2020/041793 (see also Examples 1, 2, and 4, incorporated herein by reference), using an initial quantity of 1 g of transcribed mRNA.

Example 3: Enzymatic Digestion and Affinity Chromatography Method

Enzymatic Digestion and Filtration

Serine protease (550 Units; ArcticZymes ref. 71600-110) was added directly to the mixture and the solution was stirred at 37° C. for 2 hours. The reaction was quenched by dilution with DTT solution to a final concentration of 55 mM DTT.

The whole volume was then introduced in a Kr2i TFF system (Repligen) equipped with a 100 kDa modified polyethersulfone (mPES) hollow fiber (Repligen), 0.5 mm lumen, 41.5 cm height at a shear rate of $700s^{-1}$. A TMP between 7 to 9 psi (about 0.48 bar to about bar) was maintained and conductivity monitored. The product was initially concentrated to 10-12 mg/mL, followed by a diafiltration with 50 mM Tris, 150 mM NaCl, 55 mM DTT, pH 8, then 50 mM Tris, 150 mM NaCl, pH 8 and, to finish, water for injection. The entire product was harvested, and the fiber rinsed with water for injection and pooled with the product. mRNA yield after concentration and diafiltration was at least 90%. mRNA yield was unchanged when a 300 kDa filter was used in place of a 100 kDa filter (i.e., at least 90%).

Concentration was adjusted to 4 g/L prior to performing the capping reaction (described above).

Affinity Chromatography and Filtration

After capping, the reaction was diluted 4-fold with injection (loading) buffer (50 mM sodium phosphate, 1070 mM sodium chloride, 5 mM EDTA, pH 7) and injected on an AKTA™ Avant 150 equipped with a HiScale™ 50/40 column (GE Healthcare) packed with oligo(dT)$_{25}$ resin. Thus, the final concentration of sodium chloride in the mRNA preparation for injection was 800 mM. The column volume was 0.433 L, and ran between 244 and 422 cm/h. After injection, the column was washed three times, respectively with 50 mM sodium phosphate, 800 mM NaCl, 5 mM EDTA, pH 7; 50 mM sodium phosphate, 400 mM NaCl, 5 mM EDTA, pH7; 50 mM sodium phosphate, 5 mM EDTA, pH 7, then eluted with nuclease free water. The only peak was collected in a sterile bottle then transferred into the Kr2i TFF system equipped with a 50 kDa mPES hollow fiber (Repligen), 0.5 mm lumen, 41.5 cm height at a shear rate of $700s^{-1}$. A TMP between 7 to 9 psi (about 0.48 bar to about 0.62 bar) was maintained and conductivity monitored. The product was initially concentrated to mg/mL, followed by a diafiltration with nuclease free water for injection. The product was harvested and the fiber rinsed twice before pooling the harvest and the rinse fractions. The concentration was adjusted to 1 g/L before being filtered on a PES 0.22 µm filter that had previously undergone gamma irradiation.

Example 4: Full Enzymatic Method

First Enzymatic Digestion and Filtration

Serine protease (550 Units; ArcticZymes ref. 71600-110) was added directly to the mixture and the solution was stirred at 37° C. for 2 hours. The reaction was quenched by dilution with DTT solution to a final concentration of 55 mM DTT.

The whole volume was then introduced in a Kr2i TFF system (Repligen) equipped with a 100 kDa mPES hollow fiber (Repligen), 0.5 mm lumen, 41.5 cm height at a shear rate of $700s^{-1}$. A TMP between 7 to 9 psi (about 0.48 bar to about 0.62 bar) was maintained and conductivity monitored. The product was initially concentrated to 10-12 mg/mL, followed by a diafiltration with 50 mM Tris, 150 mM NaCl, 55 mM DTT, pH 8, then 50 mM Tris, 150 mM NaCl, pH 8 and, to finish, water for injection. The entire product was harvested, and the fiber rinsed with water for injection and pooled with the product. Concentration was adjusted to 4 g/L prior to performing the capping reaction (described above).

Second Enzymatic Digestion and Filtration

After capping, serine protease (550 Units; ArcticZymes ref. 71600-110) was added directly to the mixture and the solution was stirred at 37° C. for 2 hours. The reaction was quenched by dilution with DTT solution to a final concentration of 55 mM DTT.

The whole volume was then introduced in a Kr2i TFF system (Repligen) equipped with a 100 kDa modified polyethersulfone (mPES) hollow fiber (Repligen), 0.5 mm lumen, 41.5 cm height at a shear rate of $700s^{-1}$. A TMP between 7 to 9 psi (about 0.48 bar to about bar) was maintained and conductivity monitored. The product was initially concentrated to at least 2 mg/mL, followed by a diafiltration with 50 mM Tris, 150 mM NaCl, 55 mM DTT, pH 8, then 50 mM Tris, 150 mM NaCl, pH 8 and, to finish, water for injection. The entire product was harvested, and the fiber rinsed twice with water for injection and pooled with the product. Concentration was adjusted to 1 g/L prior to being filtered on a PES 0.22 µm filter that had previously undergone gamma irradiation. To finish the product is stored at −20° until formulation.

Example 5: Analysis of Purified mRNA

The quality of the purified mRNA was assessed by several metrics, including by capillary gel electrophoresis (CGE) to measure mRNA integrity and by known techniques to measure percent capping (Cap 1), poly(A) tail length, and total mRNA length (see Tables 1-2). The electropherogram of the mRNA purified by the enzymatic/affinity and full enzymatic methods was consistent with expectations. No significant shoulder was observed (data not shown), thereby indicating that these methods did not adversely impact mRNA quality and integrity. mRNA integrity at 5° C. was evaluated over time by capillary electrophoresis (CE).

The presence of proteins (e.g., IVT enzymes, proteinase, or capping enzymes) was analyzed in samples taken at various stages of the method. Samples were loaded onto a 4-15% Criterion™ TGX™ SDS-PAGE gel (Bio-Rad) and the gel was silver stained. Prior to loading on the gel, samples were treated with RNAse A to remove RNA.

Results and Discussion

The steps of the enzymatic/affinity method and the full enzymatic method are summarized in FIG. 1. In the enzymatic/affinity and full enzymatic methods, serine protease was used after the IVT/DNase steps to digest enzymes involved in the enzymatic steps, and the resulting peptides were then eliminated from the mixture by TFF. For the enzymatic/affinity method, after the capping step, resin supporting poly dT ligand was used to capture the mRNA due to its affinity with the poly-A tail. The enzymatic/affinity method uses an orthogonal purification strategy: impurities are eliminated from the mixture first, then the mRNA is captured using one of its properties (e.g., poly-A tail).

mRNA at a 1 g scale was purified by all three methods, and the results are summarized in Table 1 below. The mRNA obtained with the enzymatic/affinity method and the full enzymatic method had comparable characteristics as mRNA obtained from the ethanol method. mRNA size and tail length were consistent with expectations. The cap percentage was also consistent with expectations, indicating that the enzymatic/affinity and full enzymatic methods did not adversely affect the capping reaction.

TABLE 1

Results of 1 g scale batches of mRNA purified by the ethanol-based method, the enzymatic/affinity method, and the full enzymatic method.

| | Test | Spec. | Ethanol-based Method | Full Enzymatic Method | Enzymatic/ Affinity Method |
|---|---|---|---|---|---|
| | Yield (1 g scale) | 1.0 g | 0.73 g-0.80 | 0.84 g | 0.87 g |
| | Number of batches | — | 4 | 1 | 1 |
| mRNA CHARACTERISTICS | mRNA integrity (CGE) | >60% | 89%-91% | 83% | 86% |
| | % capping | >90% | 97%-99% | 98% | 98% |
| | poly(A) tail length | >100 nt | 179-180 | 193 | 192 |
| | mRNA total length (Capillary electro.) | 1600-2200 nt | 1834-1934 | 1965 | 1981 |
| PURITY | dsRNA | — | <0.1% | <0.1% | <0.1% |
| | Residual IVT enzymes | no residual enzymes | None | None | None |
| | RNAse | no RNAse | Negative | Negative | Negative |
| | Residual solvent (EtOH) | <5000 ppm (EtOH) | <5000 ppm | NA | NA |

NA: not applicable

The cycle time of the ethanol method, the enzymatic/affinity method, and the full enzymatic method were compared. For the ethanol method, the total time for the IVT reaction and purification steps was about 10 hours and 45 minutes. The same steps in the enzymatic/affinity method and the full enzymatic method each took about 9 hours and 45 minutes. The total time for the capping/purification/filtration/repartition steps for the ethanol method was about 11 hours and 45 minutes, whereas the same steps for the enzymatic/affinity method and the full enzymatic method were 10 hours and 30 minutes and 10 hours and 45 minutes, respectively.

Example 6: Evaluation of Residual Proteins Following Capping

Figure 2:
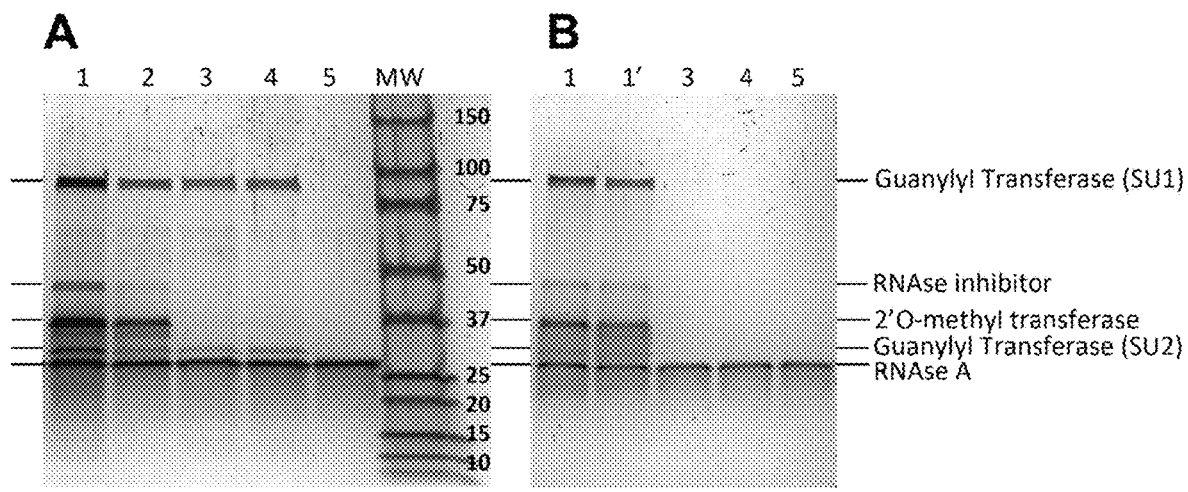
FIG. 2 shows images of silver-stained SDS-PAGE gels of proteins present at different steps of the ethanol-free purification process using the enzymatic/affinity method. Samples were taken at various points following capping. The enzymatic/affinity method was performed without (panel A) or with (panel B) an intermediate frontal filtration step prior to affinity chromatography. In both panels, lane 1 corresponds to the product obtained immediately after capping, lane 3 corresponds to affinity chromatography eluate, lane 4 corresponds to TFF eluate, lane 5 corresponds to the product obtained after final frontal filtration. MW: molecular weight marker. Sizes of the molecular weight marker are shown to the right, in kDa. SU: subunit. In panel A, lane 2 corresponds to affinity chromatography flow through. In panel B, lane 1' corresponds to product obtained after an intermediate step of frontal filtration, performed after capping and prior to affinity chromatography. Proteins used in capping are shown along with RNAse A. It was observed that affinity chromatography did not completely remove guanylyl transferase (GuaT) when this step was performed directly after capping. In contrast, the RNA product was free of enzymes after the affinity chromatography step when intermediate step of frontal filtration was performed.

Following in vitro transcription and enzymatic digestion to remove contaminating proteins, additional proteins are introduced into the mRNA product to perform capping. The presence of proteins introduced in the capping reaction was evaluated at various points downstream of the capping reaction using silver-stained SDS-PAGE gels. It was observed that while RNAse inhibitor and 2'O-methyl transferase were no longer detectable following affinity chromatography, both subunits of guanylyl transferase (GuaT) remained present (see FIG. 2, lane 4 of panel A). However, GuaT was no longer detectable following frontal filtration on a 0.22 µm PES filter (see see FIG. 2, lane 5 of panel). The incorporation of an intermediate frontal filtration step on a 0.22 µm PES filter notably reduced the amount of contaminating GuaT protein from the affinity chromatography step (see FIG. 2, lane 1' of panel B). The use of an intermediate frontal filtration step (i.e., prior to affinity chromatography) advantageously reduces the protein load applied to the affinity chromatography column and that is carried over in downstream steps (e.g. TFF). The incorporation of a frontal filtration step prior to affinity chromatography was evaluated at both the 1 g and 10 g scale and yielded similar results.

Example 7: Evaluation of Enzymatic Digestion Conditions

Various concentrations of proteinase K (Sigma, ref. P2308) were tested, and protein digestion was evaluated using silver-stained SDS-PAGE gels.

Figure 3:
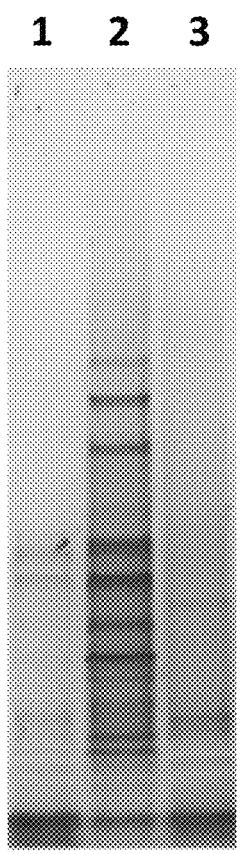
FIG. 3 shows an image of a silver-stained SDS-PAGE gel of an IVT reaction treated with different proteinase conditions. Lane 1: treatment with serine proteinase (ArcticZymes) at 0.55 U/mg RNA, 2 h incubation; lane 2: treatment with serine proteinase (ArcticZymes) at 0.05 U/mg RNA, 2 h incubation; lane 3: treatment with proteinase K (Sigma) at 0.025 U/mg RNA, 30 min incubation.

As shown in FIG. 3, the digestion obtained with proteinase K (Sigma) at 0.025 U/mg RNA following a 30-minute incubation was comparable to the digestion obtained with serine proteinase (ArcticZymes) at 0.55 U/mg RNA following a 2 h incubation (compare lanes 1 and 3 of FIG. 3). In contrast, the digestion obtained with serine proteinase (ArcticZymes) at 0.05 U/mg RNA following a 2 h incubation was incomplete (see lane 2 of FIG. 3). Thus, the duration of the enzymatic digestion could be reduced 4-fold, while also using 22-fold less proteinase, when using proteinase K (Sigma). Downstream capping was comparable between all three conditions. These results validate the use of proteinase from various providers. Both enzyme concentration and the duration of the enzymatic digestion may notably be reduced when using proteinase K. This advantageously further reduces the cycle time of the method.

Example 8: Evaluation of Buffer Conditions

Figure 4:
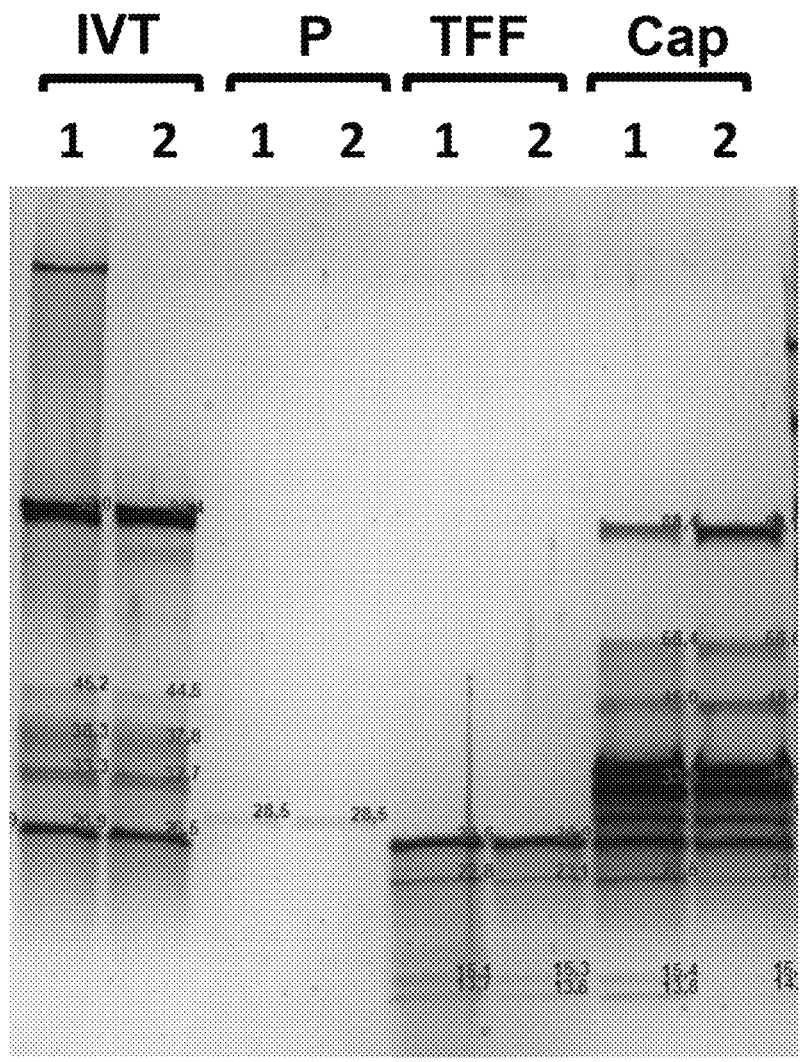
FIG. 4 shows an image of a silver-stained SDS-PAGE gel of proteins present at different steps of the ethanol-free purification process. Specifically, samples were taken after in vitro transcription (lanes: IVT), after treatment with proteinase K (Sigma) (lanes: P), after TFF and before capping (lanes: TFF), or after capping (lanes: Cap). Tris NaCl buffer was used for diafiltration in presence of DTT (condition 1) or absence of DTT (condition 2).

Following a 30 min enzymatic digestion with proteinase K (Sigma) at 0.025 U/mg RNA, TFF was performed. Different diafiltration buffer conditions were evaluated. In particular, 50 mM Tris, 150 mM NaCl buffer was used for diafiltration in presence of DTT (55 mM) or absence of DTT. Profiles were similar between buffer conditions (see FIG. 4, compare conditions 1 and 2). In addition, capping was comparable when using either buffer (i.e., 93.1% of Cap 1 when using Tris NaCl DTT buffer, 95.5% of Cap 1 when using Tris NaCl buffer. Thus, the presence of DTT in the buffer was not required.

Example 9: Scale-Up mRNA at 10 g and 20 g scale was purified with the enzymatic/affinity method, and the results are summarized in Table 2 below. Scaling up the purification was successfully performed. The analytical profile was acceptable. Residual GuaT was eliminated with intermediate frontal filtration, with a 0.2 µm PES filter.

Figure 5:
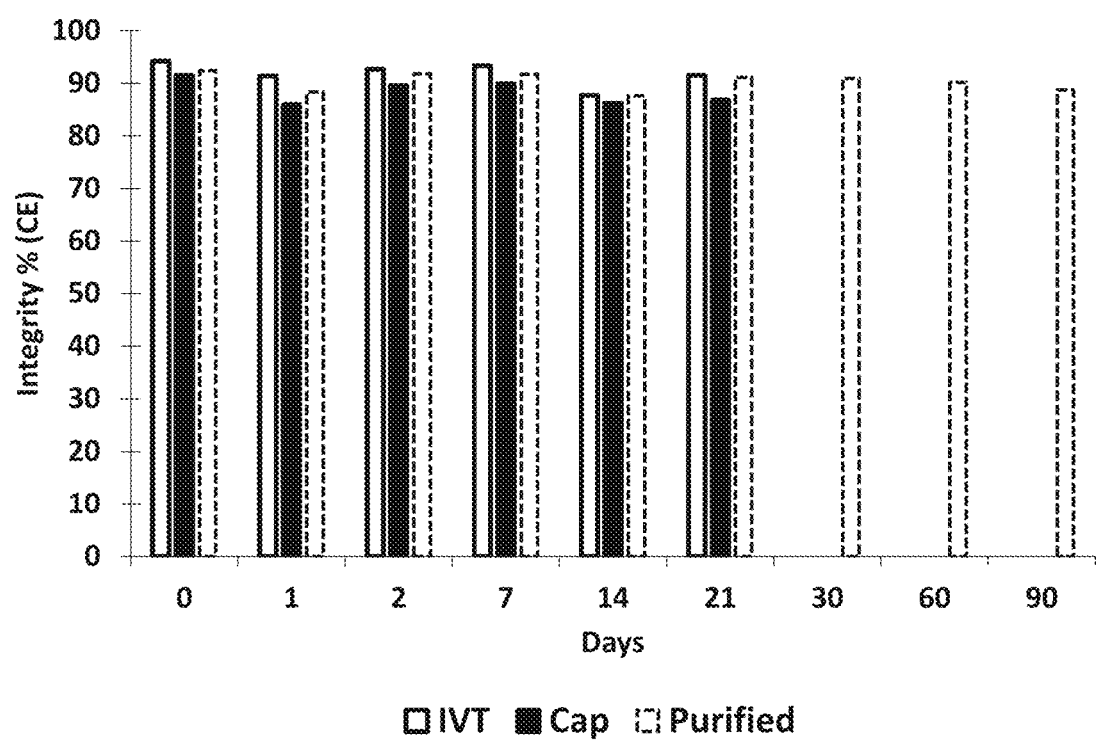
FIG. 5 shows a diagram depicting the integrity of purified mRNA and intermediates over time at +5° C. Samples were aliquoted after IVT (white bars), after capping (black bars), and after complete mRNA purification using the enzymatic/affinity method (dashed bars), stored at +5° C., and mRNA integrity analyzed by capillary electrophoresis (CE) at different time points. The integrity of the mRNA in the IVT reaction was stable at +5° C. for at least 21 days with no significant decrease in integrity over time. The integrity of the mRNA obtained after capping was >85% at 21 days with no significant decrease in integrity over time. Purified mRNA was stable at +5° C. for at least 3 months with no significant decrease in integrity over time. Advantages of having RNA that is stable at +5° C. notably include ease of storage of the product (i.e., in a cold room rather than a −20° C. freezer) and the absence of thawing constraints in the downstream process.

The evolution of the integrity of mRNA purified with the enzymatic/affinity method over time was assessed, as illustrated in FIG. 5.

TABLE 2

Results of 10 g and 20 g scale batches of mRNA purified by the enzymatic/affinity method.

| | Test | Results | |
|---|---|---|---|
| mRNA CHARACTERISTICS | Scale | 10 g | 20 g |
| | Yield | 11.2 g | 20.5 g |
| | mRNA integrity (CGE) | 92% | 92% |
| | % capping | 94% | 96% |
| | poly(A) tail length | 118 | NA |
| | mRNA total length (Capillary electro.) | 1938 | 1926 |
| PURITY | dsRNA | <0.1% | <0.1% |
| | Residual pDNA | 0.1 pg/mL | 0.2 pg/mL |
| | Residual process enzymes (SDS-PAGE) | None | None |
| | Endotoxin level (LAL) | <0.250 UI/mL | <0.260 UI/mL |
| | RNAse | Negative | Negative |

NA: not available mRNA at a 100 g scale was also successfully purified by enzymatic/affinity method. It was found that the 100 g batch meets all the acceptance criteria.

Overall, the enzymatic/affinity method and the full enzymatic method result in high yields of isolated purified mRNA, and the yields are similar or better to that of the ethanol-based method. Additionally, the overall time of the enzymatic/affinity method and the full enzymatic method is reduced compared to the ethanol method.

The enzymatic/affinity method and the full enzymatic method advantageously do not require ethanol, which is highly flammable and dangerous to work with when performing commercial scale mRNA production.

Example 10: Process Optimization—mRNA Solubilization

While no precipitate was observed during mRNA purification with a first mRNA construct (referred to hereinafter as Construct 1), used in the previous examples, the formation of a precipitate could be observed during in vitro transcription of a second construct (Construct 2). This indicates that a precipitate may form during large-scale purification of mRNA in some instances, which can have a negative impact on downstream steps, in particular on downstream filtration, as the precipitate may clog the filter.

The precipitate was first characterized to determine if it comprised in vitro transcribed mRNA. mRNA quantity and integrity were evaluated using ion-pair reversed-phase ultra high-performance liquid chromatography (RP-IP-UPLC-UV) and capillary electrophoresis, respectively, in both the supernatant and the precipitate fractions. Prior to performing RP-IP-UPLC-UV, supernatant and precipitate were separated, and the precipitate was washed in RNase-free water and resolubilized with 1 mM HCl. The chromatographic peak corresponding to mRNA showed a surface area of 0.825 for the supernatant and a surface area of 8.416 for the precipitate, corresponding to mRNA concentrations of 0.34 mg/mL and 3.21 mg/mL, respectively. Here, approximately 90% of the mRNA detected was found to be in the precipitate. Thus, very high amounts of mRNA may precipitate out of the preparation during in vitro transcription. In contrast, precipitation did not negatively affect mRNA integrity.

In view of resolubilizing the precipitate for downstream purification, several conditions were evaluated, and the presence of precipitate determined based on the absorbance value of the solution at $A_{600\ nm}$ (Nanodrop).

Neither dilution of the precipitate in RNase-free water nor dilution of the precipitate in a Tris buffer (50 mM Tris, 150 mM NaCl, pH 7.5) resolubilized the precipitate. Reducing the pH of the solution from about 7 to 4 with a solution of 500 mM citric acid also did not resolubilize the precipitate. (Data not shown.)

Figure 6:
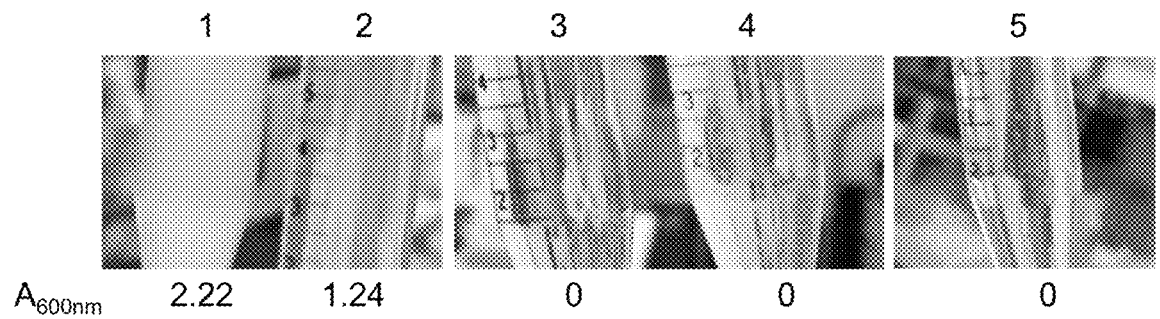
FIG. 6 shows photographs illustrating the effect of sodium citrate or EDTA on precipitate formed following large-scale in vitro transcription of mRNA. Turbidity, and thus the presence of precipitate, was determined by absorption at $A_{600\ nm}$ of preparations comprising precipitate formed following large-scale in vitro transcription of mRNA under different treatment conditions at about 37° C.) for 5 minutes. Sample 1: No treatment; 2: 10 mM sodium citrate; 3: 25 mM sodium citrate; 4: 50 mM sodium citrate; 5: 25 mM EDTA.

Surprisingly, the precipitate was successfully resolubilized by addition of sodium citrate or EDTA to the preparation, as illustrated in FIG. 6. A 5-min incubation time was sufficient for complete solubilization at 35° C., indicating that precipitate formation is not irreversible and that it can be quickly resolubilized.

Thus, the addition of sodium citrate or EDTA to a preparation comprising in vitro transcribed mRNA advantageously resolubilizes any precipitated mRNA prior to performing downstream filtration steps.

Example 11: Process Optimization—Oligo dT Loading Buffer

Additional analyses were performed on mRNA purified at a 10 g or 20 g batch scale (Construct 1). Specifically, mRNA integrity as well as the presence dsRNA and residual plasmid DNA were evaluated directly after capping or a first TFF step and also directly after the affinity chromatography step. The presence of dsRNA was detected by ELISA using the J2 monoclonal antibody. The presence of residual DNA was detected by qPCR.

TFF and affinity chromatography were performed as described in Example 3 above. The oligo dT resin was loaded with a preparation comprising 2 mg/mL mRNA, 800 mM NaCl, 30 mM Tris, 8 mM EDTA, pH 7.4. Washing was performed with the same solution but comprising only 100 mM NaCl.

Figure 7:
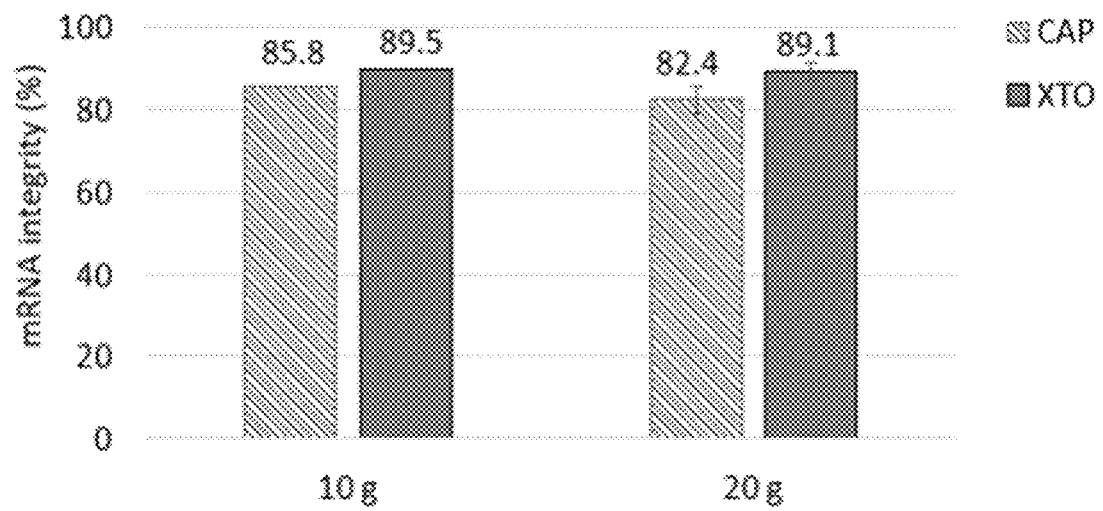
FIG. 7 shows a diagram depicting the integrity of mRNA after capping (CAP) and after oligodT affinity chromatography (XTO) for large scale mRNA purification as determined by capillary electrophoresis. Results are shown for a 10 g batch and for an average of 3 replicates of a 20 g batch. mRNA integrity increased following completion of the affinity chromatography step.
Figure 8:
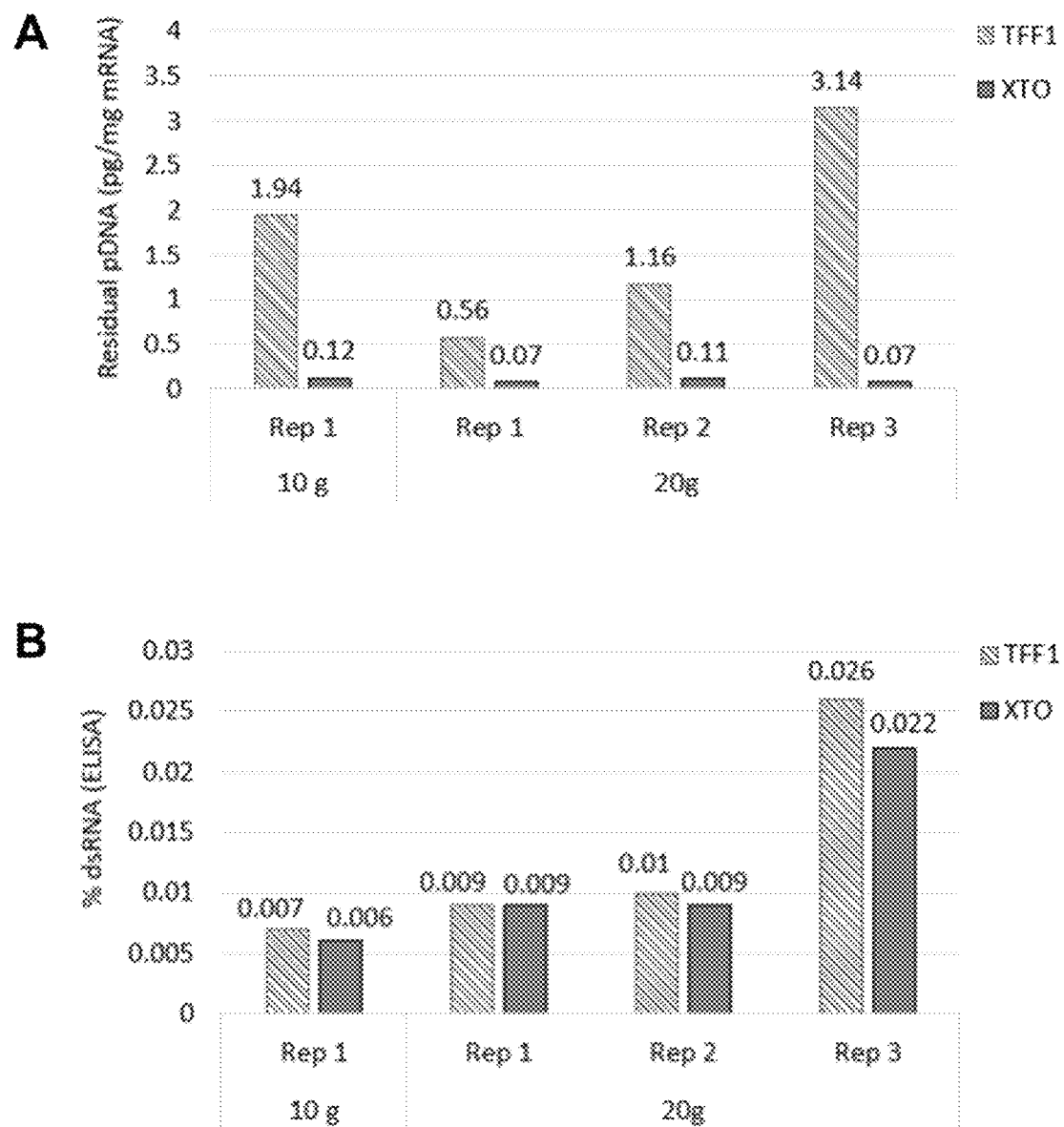
FIG. 8 shows a diagram depicting (A) the amount of residual plasmid DNA and (B) the percent of RNA that is double-stranded RNA (dsRNA) after a first tangential flow filtration step (TFF1) and after oligodT affinity chromatography (XTO) for large scale mRNA purification as determined by qPCR and ELISA, respectively. Results are shown for a 10 g batch and for 3 independent replicates of a 20 g batch (Rep 1, Rep 2, Rep 3). A highly pure mRNA sample is obtained following TFF and oligo dT affinity chromatography for both the 10 g and 20 g batch sizes.

95%-100% of mRNA was recovered after affinity chromatography. Furthermore, mRNA integrity was increased (FIG. 7) and low levels of residual plasmid DNA contamination and dsDNA contamination were observed for all batches following TFF and affinity chromatography (FIG. 8).

Thus, large scale purification of mRNA results in highly pure mRNA having excellent quality attributes following the affinity chromatography step.

Precipitation was unexpectedly observed for two other mRNA constructs when conditions were adjusted for loading onto the oligo dT resin as described above, which led to clogging of the column.

Figure 9:
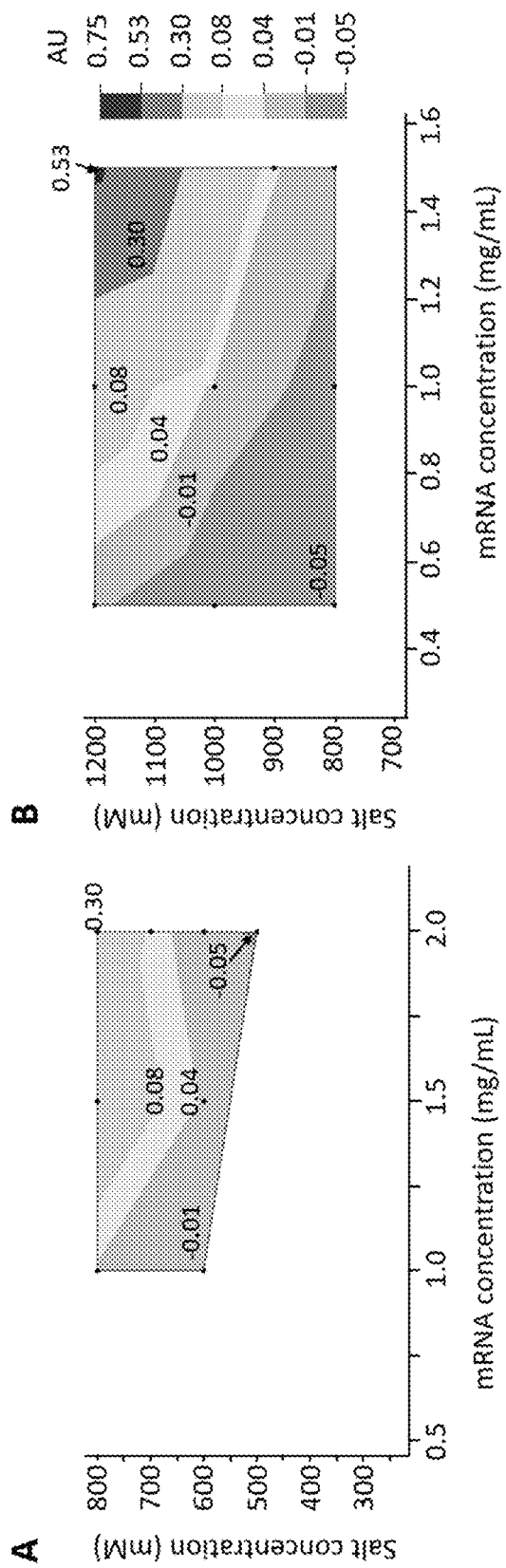
FIG. 9 shows a diagram depicting contour plots of salt concentration as compared to mRNA concentration for mRNA construct 2 after a 2 h incubation in (A) NaCl or (B) KCl. The presence of precipitate was measured by UV spectrometry using UV-Vis 600 nm absorbance values and is expressed in absorbance units (AU). A negative AU value was equivalent to an absorbance of 0 and indicated a limpid solution. An AU value of at least 0.05 indicated a risk of precipitate formation; precipitate was visible to the naked eye in the form of cloudiness at AU values of at least 0.3. The use of KCl reduced precipitate formation at high salt concentrations when compared to NaCl at the same mRNA concentration.
Figure 10:
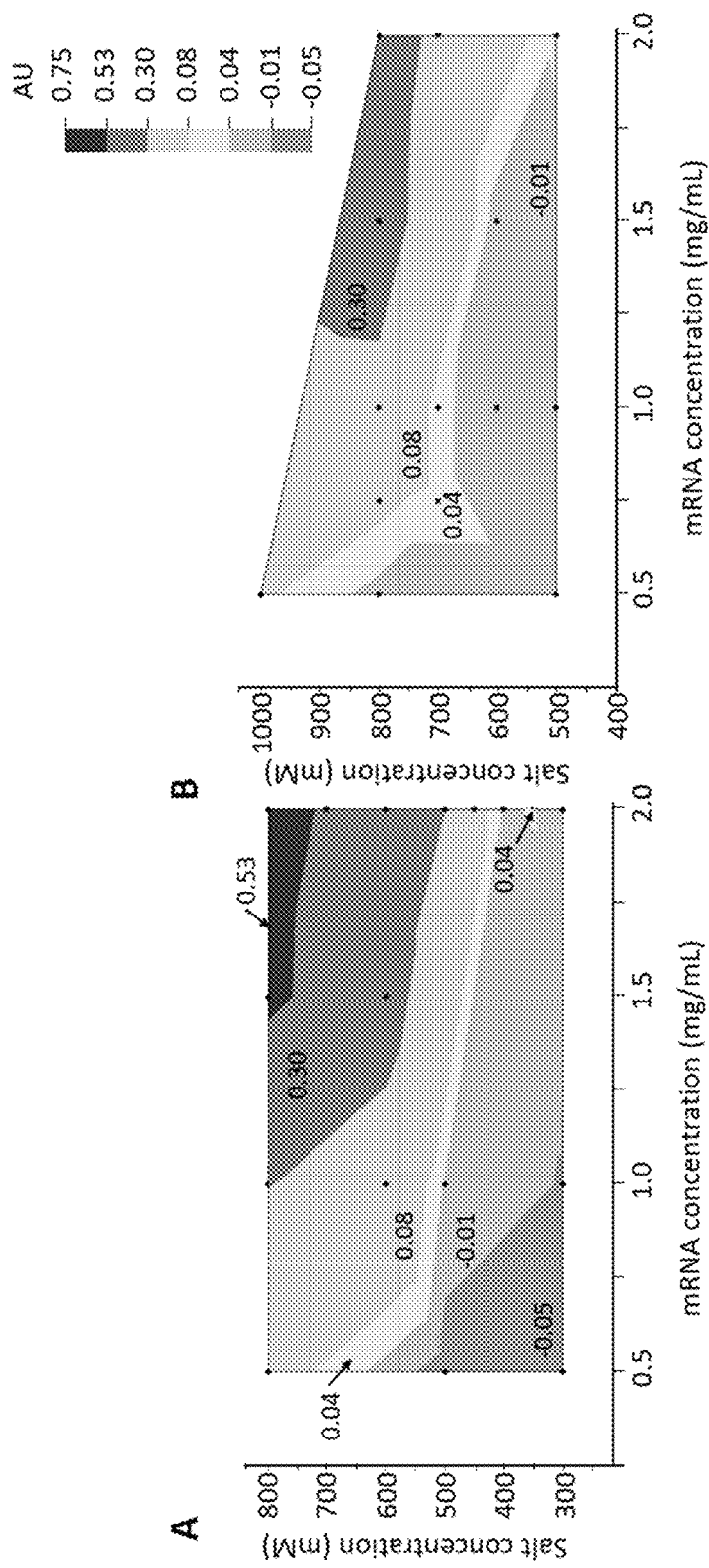
FIG. 10 shows a diagram depicting contour plots of salt concentration as compared to mRNA concentration for mRNA construct 3 after a 2 h incubation in (A) NaCl or (B) KCl. The presence of precipitate was measured by UV spectrometry using UV-Vis 600 nm absorbance values and is expressed in absorbance units (AU) as described above for FIG. 9. The use of KCl reduced precipitate formation at high salt concentrations when compared to NaCl at the same mRNA concentration.
Figure 11:
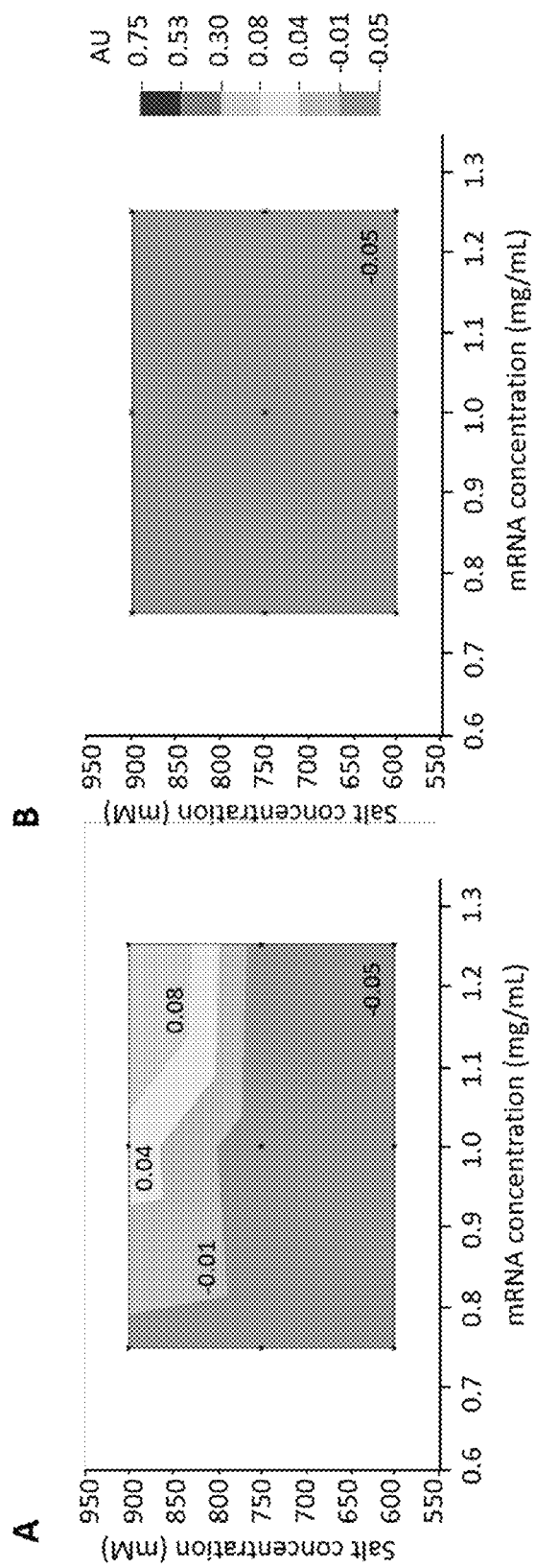
FIG. 11 shows a diagram depicting contour plots of salt concentration as compared to mRNA concentration for mRNA construct 4 after a 2 h incubation in (A) NaCl or (B) KCl. The presence of precipitate was measured by UV spectrometry using UV-Vis 600 nm absorbance values and is expressed in absorbance units (AU) as described above for FIG. 9. No precipitate was observed in any of the evaluated conditions when using KCl, in contrast to NaCl.

To determine the impact of NaCl in the loading buffer on the formation of the precipitate, various concentrations of NaCl or KCl were evaluated as a function of mRNA concentration for three different mRNA constructs (Constructs 2-4). Specifically, precipitation was monitored by UV (Nanodrop) using UV-Vis $A_{600\ nm}$ absorbance values after 2 h incubation of mRNA with the salt and results were provided on contour plots (FIGS. 9-11). A negative AU value was equivalent to an absorbance of 0 and indicated a limpid solution. An AU value of at least 0.05 indicated a risk of precipitate formation; precipitate was visible to the naked eye in the form of cloudiness at AU values of at least 0.3.

As shown in FIGS. 9-11, the formation of precipitate was reduced over a greater range of KCl concentrations as compared to NaCl concentrations at a given mRNA concentration. In particular, mRNA did not precipitate at higher KCl concentrations for these three constructs. Thus, KCl represents an advantageous alternative to NaCl in cases where precipitation occurs prior to affinity chromatography, as higher concentrations may be used.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

All patents and publications cited herein are incorporated by reference herein in their entirety.

The invention claimed is:

1. A method of purifying messenger RNA (mRNA), comprising:
   (a) subjecting a preparation comprising in vitro synthesized mRNA to an enzymatic digestion with a proteinase;
   (b) subjecting the preparation obtained from step (a) to a step of tangential flow filtration (TFF);
   (c) subjecting the preparation obtained from step (b) to a step of capping;
   (d) subjecting the preparation obtained from step (c) to a step of frontal filtration;
   (e) subjecting the preparation obtained from step (d) to an oligo dT affinity chromatography; and (f) subjecting the preparation obtained from step (e) to a step consisting of TFF, thereby purifying the mRNA.

2. The method of claim 1, wherein the method further comprises a step of subjecting the preparation to a step of frontal filtration after step (f).

3. The method of claim 1, wherein the frontal filtration uses a 0.2 µm filter.

4. The method of claim 1, wherein the frontal filtration reduces guanylyltransferase (GuaT) content.

5. The method of claim 1, wherein the in vitro synthesized mRNA is purified at a scale of or greater than about 100 milligram, 1 gram, 10 gram, 20 gram, 50 gram, 100 gram or more per batch.

6. The method of claim 1, wherein the in vitro synthesized mRNA is purified at a scale of or greater than about 10 gram per batch, and wherein:
(i) the purified mRNA contains less than about 1% by weight of enzyme reagents used in in vitro synthesis; and/or
(ii) the purified mRNA has an integrity greater than about 80%.

7. The method of claim 1, wherein the in vitro synthesized mRNA is purified at a scale of or greater than about 20 gram per batch, and wherein:
(i) the purified mRNA contains less than about 1% by weight of enzyme reagents used in in vitro synthesis; and/or
(ii) the purified mRNA has an integrity greater than about 80%.

8. The method of claim 1, wherein the purified mRNA is suitable for therapeutic use.

9. The method of claim 1, wherein the method does not include any additional affinity chromatography steps.

10. The method of claim 1, wherein the proteinase comprises a serine protease.

11. The method of claim 1, wherein the preparation comprising in vitro synthesized mRNA is incubated with the proteinase at about 37° C. for at least 30 minutes.

12. The method of claim 1, wherein the proteinase is inactivated with a reducing agent.

13. The method of claim 1, wherein the TFF uses an about 50 kDa to about 300 kDa cut-off filter.

14. The method of claim 1, wherein the capping is performed at about 37° C. for at least 30 minutes.

15. The method of claim 1, wherein the method is further subjected to a step of tailing with a poly(A) polymerase to produce a poly(A) tailed mRNA prior to the oligo dT affinity chromatography.

16. The method of claim 15, wherein the tailing is performed prior to capping.

17. The method of claim 15, wherein the tailing is performed concomitantly to capping.

18. The method of claim 15, wherein the tailing is performed after capping.

19. The method of claim 6, wherein:
(i) residual plasmid DNA in the purified mRNA is less than or equal to about 0.2 pg/mg; and/or
(ii) the purified mRNA contains less than about 0.1% by weight of double-stranded RNA (dsRNA).

20. The method of claim 7, wherein:
(i) residual plasmid DNA in the purified mRNA is less than or equal to about 0.2 pg/mg; and/or
(ii) the purified mRNA contains less than about 0.1% by weight of double-stranded RNA (dsRNA).

21. The method of claim 12, wherein the reducing agent is dithiothreitol (DTT).

* * * * *